(12) United States Patent
Khanmamedova et al.

(10) Patent No.: US 6,794,332 B2
(45) Date of Patent: Sep. 21, 2004

(54) HIGHLY SELECTIVE SHELL IMPREGNATED CATALYST OF IMPROVED SPACE TIME YIELD FOR PRODUCTION OF VINYL ACETATE

(75) Inventors: Alla Konstantin Khanmamedova, Sugar Land, TX (US); Binghui Li, Sugar Land, TX (US); Robin J. Bates, Stafford, TX (US); Yuangen Ken Yin, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 42 days.

(21) Appl. No.: 10/210,294

(22) Filed: Jul. 31, 2002

(65) Prior Publication Data

US 2003/0148883 A1 Aug. 7, 2003

Related U.S. Application Data

(63) Continuation-in-part of application No. 10/174,642, filed on Jun. 19, 2002, which is a continuation of application No. 09/612,159, filed on Jul. 7, 2000, now Pat. No. 6,420,308.

(51) Int. Cl.[7] .......................... B01J 23/02; B01J 23/04; B01J 23/58; B01J 23/42; B01J 23/44
(52) U.S. Cl. ..................... 502/344; 502/330; 502/339
(58) Field of Search ................................. 502/330, 339, 502/344

(56) References Cited

U.S. PATENT DOCUMENTS

| | | | |
|---|---|---|---|
| 4,048,096 A | | 9/1977 | Bissot |
| 4,937,219 A | * | 6/1990 | Haruta et al. ............... 502/174 |
| 5,179,056 A | | 1/1993 | Bartley |
| 5,179,057 A | * | 1/1993 | Bartley ....................... 502/170 |
| 5,189,004 A | | 2/1993 | Bartley |
| 5,274,181 A | | 12/1993 | Bartley et al. |
| 5,314,858 A | | 5/1994 | Colling |
| 5,332,710 A | | 7/1994 | Nicolau et al. |
| 5,342,987 A | | 8/1994 | Bartley |
| 5,567,839 A | | 10/1996 | Gulliver et al. |
| 5,693,586 A | | 12/1997 | Nicolau et al. |
| 6,350,901 B1 | * | 2/2002 | Kitchen et al. ............. 560/245 |
| 6,420,308 B1 | | 7/2002 | Khanmamedova |
| 6,448,432 B2 | * | 9/2002 | Williams .................... 560/245 |
| 6,579,824 B1 | * | 6/2003 | Herzog et al. .............. 502/302 |

* cited by examiner

*Primary Examiner*—Mark L. Bell
*Assistant Examiner*—Patricia L. Hailey
(74) *Attorney, Agent, or Firm*—Jim Wheelington

(57) ABSTRACT

A shell impregnated catalyst of Pd—Au produced on a silica support by impregnating the support with aqueous solutions of palladium and gold salts or acids and thereafter precipitating water insoluble compounds of Pd and Au on the support with alkali metal silicate or hydroxide fixing agents, then drying the support which has precipitated compounds of Pd and Au on its surface and reducing the surface precipitated compounds of Pd and Au until substantially all of the Pd and Au contents are reduced to a free metal state, after which the catalyst precursor is impregnated with potassium acetate and then dried. Improvements in the catalyst are realized by certain factors in process and composition.

42 Claims, 4 Drawing Sheets

Figure 1:
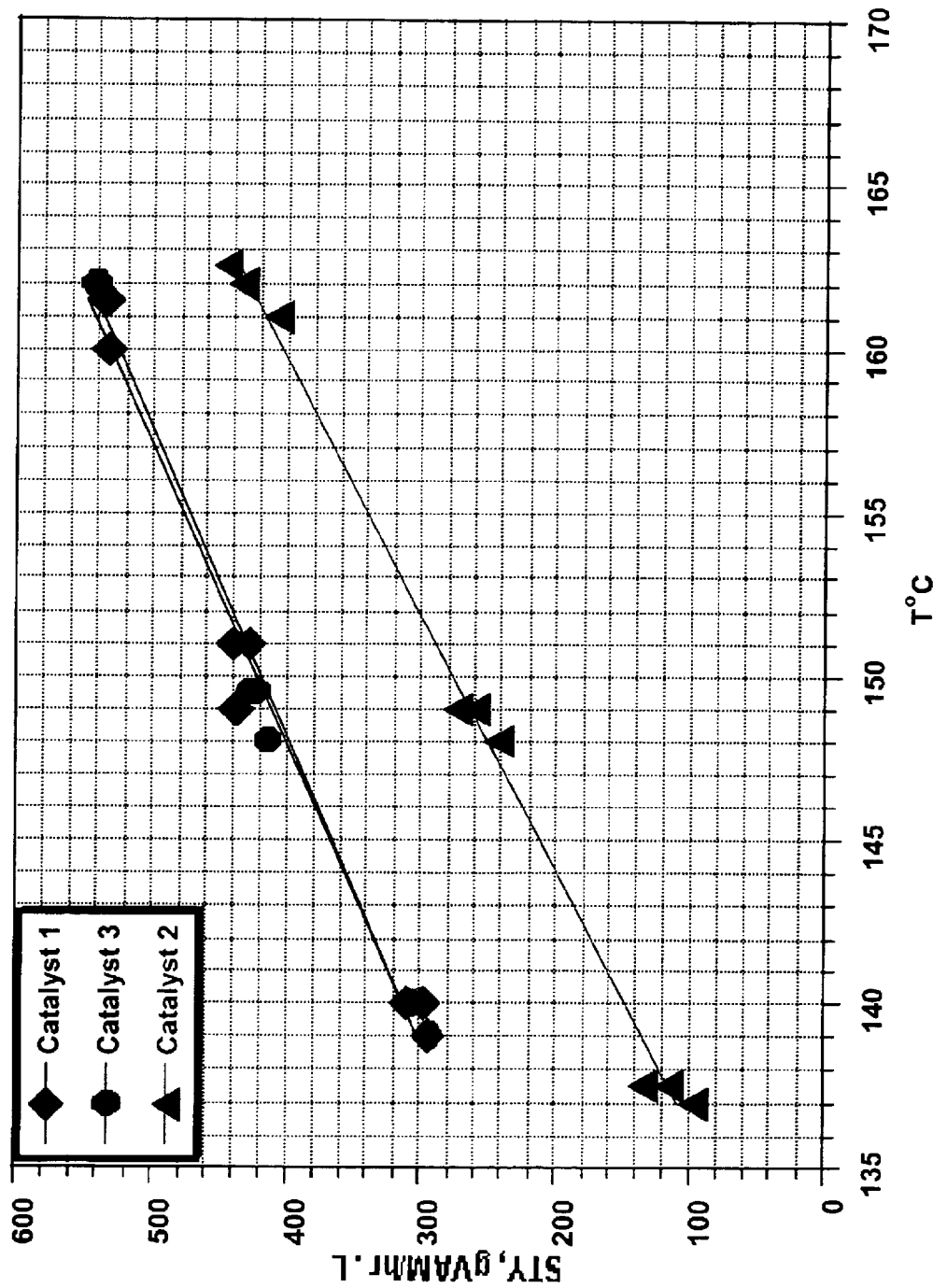
Figure 2:
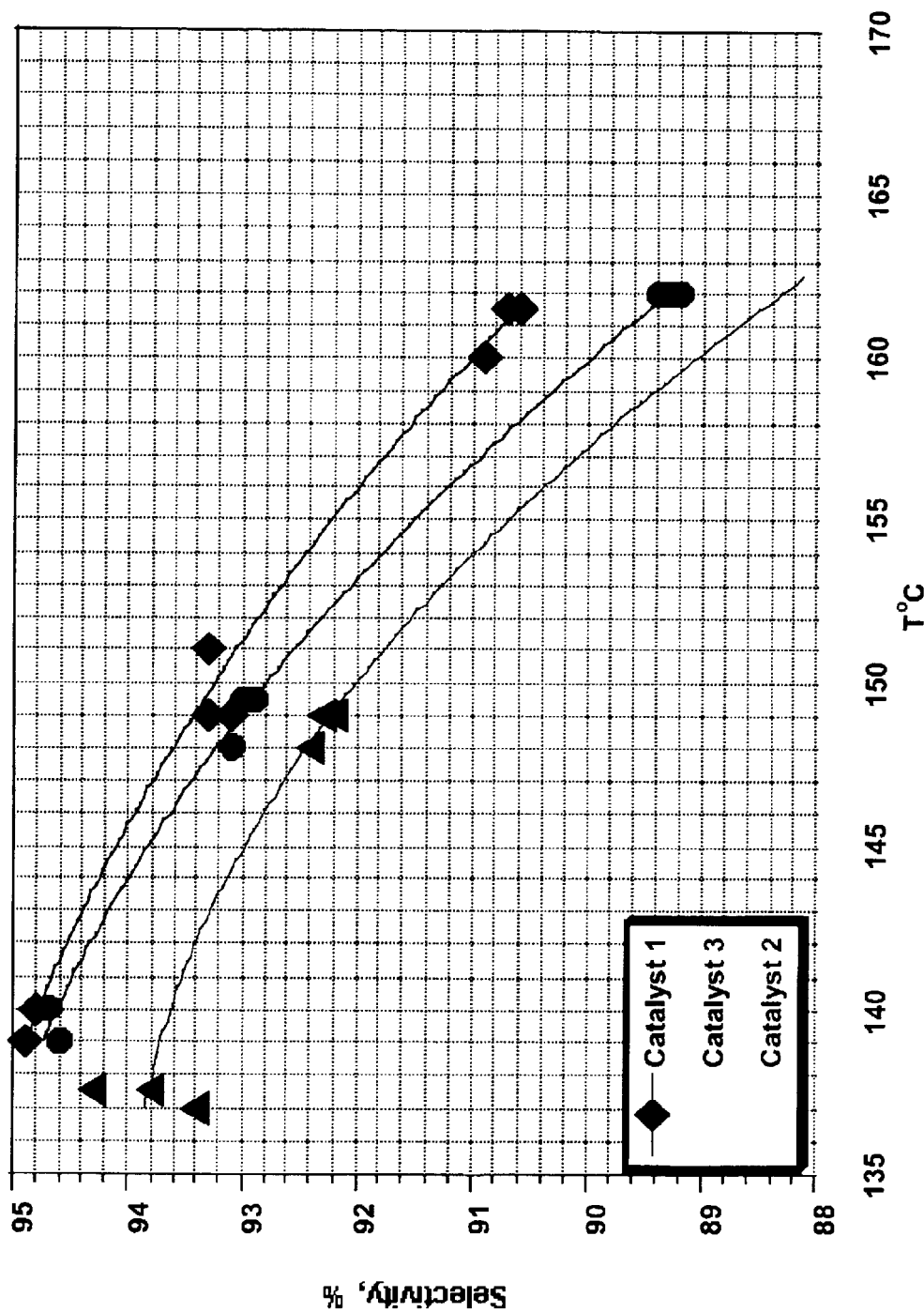
Figure 3:
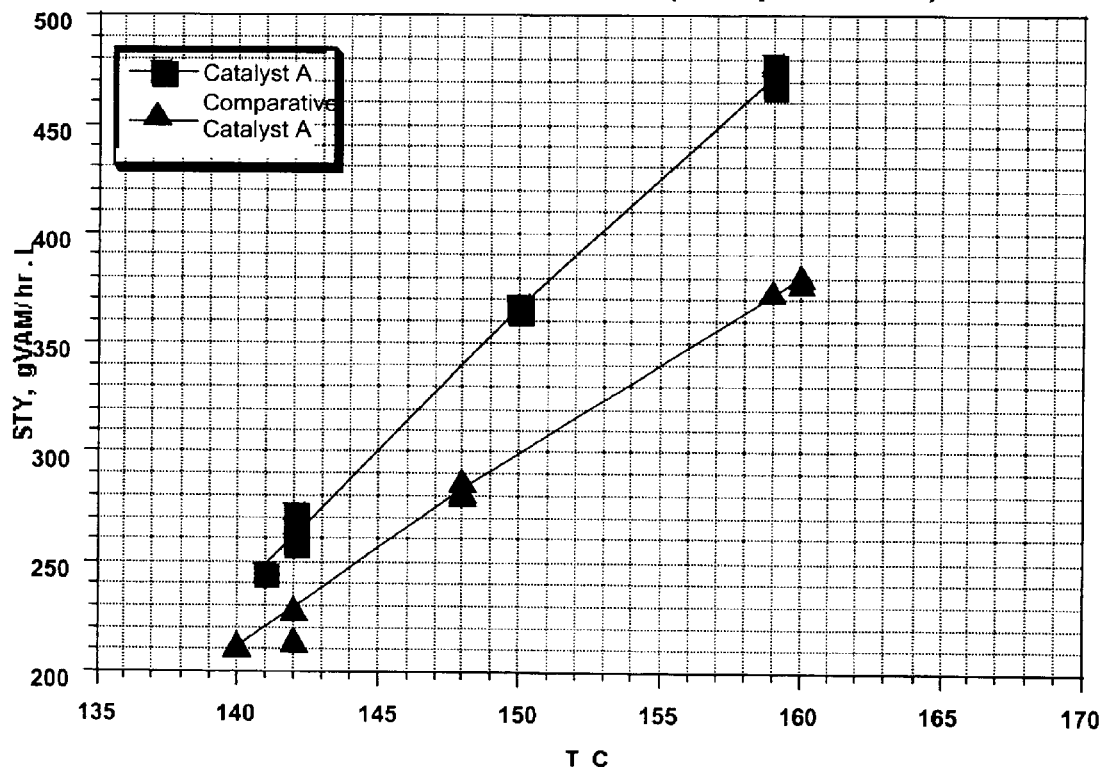
Figure 4:
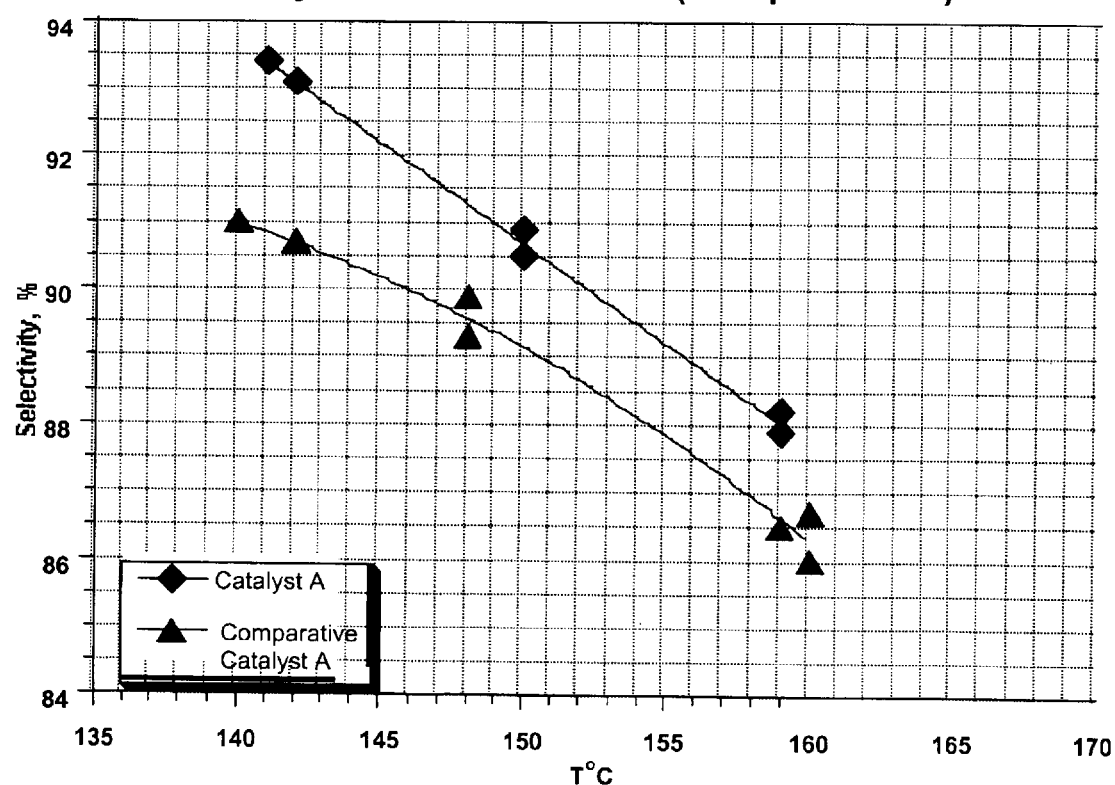

Activity performance for catalysts with/without N2 treatment prior to reduction

Selectivity comparison for catalyst washed - reduced (A) catalyst reduced - washed (Comparative A).

HIGHLY SELECTIVE SHELL IMPREGNATED CATALYST OF IMPROVED SPACE TIME YIELD FOR PRODUCTION OF VINYL ACETATE

CROSS-REFERENCE TO RELATED APPLICATIONS

This patent application is a continuation-in-part of copending U.S. patent application Ser. No. 10/174,642, filed Jun. 19, 2002, which is a continuation of U.S. Pat. No. application Ser. No. 09/612,159, filed Jul. 7, 2000, and issued as U.S. Pat. No. 6,420,308 on Jul. 16, 2002.

STATEMENT REGARDING FEDERALLY SPONSORED RESEARCH

Not applicable.

BACKGROUND OF THE INVENTION

1. Field of the Invention

This invention relates to shelled Pd—Au catalyst of particular characteristics, and methods for their production, which are effective for catalyzing the vapor phase reaction of an alkene (such as ethylene) with an alkanoic acid (such as acetic acid) and oxygen to produce an alkenyl alkanoate (such as vinyl acetate) at high values for space-time yield, specific activity, and with a high selectivity for conversion of the alkene to the alkenyl alkanoate (such as ethylene to vinyl acetate).

2. Description of the Related Art

Vinyl acetate (VA) is a commodity chemical in high demand as a monomer for production of poly(vinyl acetate). This important polymer, and its derivatives, finds extensive uses as adhesives, paints and other coatings, films and laminating materials. Many techniques have been reported in the prior art for the production of VA. A chief technique is a catalyzed gas phase reaction of ethylene with acetic acid and oxygen. Today a type of catalyst widely use for this reaction is a surface shell impregnated catalyst of a type as described in U.S. Pat. No. 4,048,096 by T. C. Bissot.

Bissot's U.S. Pat. No. 4,048,096 discloses a catalyst having a specific activity of at least about 83 grams of vinyl acetate per gram of precious metal (Pd+Au) per hour measured at 150° C. and a reaction pressure of 120 psig. The catalyst consists of: (1) catalyst support particles having a particle diameter of from about 3 to about 7 mm and a pore volume of from about 0.2 to about 1.5 ml/g, (2) palladium and gold distributed in a surface layer of the catalyst support extending less than about 0.5 mm into the support, the palladium being present in an amount of from about 1.5 to about 5.0 grams per liter of catalyst, and the gold being present in an amount of from about 0.5 to about 2.25 grams per liter of catalyst, and (3) from about 5 to about 60 grams per liter of catalyst of an alkali metal acetate. Palladium is the active catalyst metal and the gold is a catalyst promoter.

The Bissot '096 patent process for catalyst preparation comprises: (1) impregnating the catalyst support with an aqueous solution of water-soluble palladium and gold compounds, (2) precipitating water-insoluble palladium and gold compounds on the catalyst support surface by contacting the impregnated catalyst support with a solution of compounds (preferably sodium metasilicate) capable of reacting with the water-soluble palladium and gold compounds to form water-insoluble palladium and gold compounds, (3) converting the water-insoluble palladium and gold compounds into palladium and gold metal on the support surface by treatment with a reducing agent, (4) washing the catalyst with water, (5) drying the catalyst, (6) impregnating the catalyst with an alkali metal acetate promoter (e.g., a potassium promoter), and (7) drying the catalyst.

The improvement disclosed in Bissot '096, as compared to prior Pd—Au supported catalysts, involves distributing the catalyst loading of palladium and gold as a surface layer on the catalyst support which is less than about 0.5 millimeter into the support from its surface. The impregnating step is carried out with an aqueous solution of palladium and gold compounds and the total volume of the solution is from about 95 to about 100% of the absorptive capacity of the catalyst support. The precipitating step in Bissot is carried out by soaking the wet catalyst support with a solution of an alkali metal silicate, the amount of alkali silicate being such that, after the alkali metal silicate solution has been in contact with the catalyst support for about 12 to 24 hours, the pH of said solution is from about 6.5 to about 9.5. In all examples of Bissot the reduction of the precipitated compounds to Pd and Au metals is accomplished by reaction with a hydrazine solution.

As is apparent from a reading of the Bissot patent, a major concern in this art of vinyl acetate (VA) production has always been to improve the space-time yield (STY) and also the specific activity (SA) of the catalysts. Since the description of this shell type of catalyst by Bissot others have attempted to improve the catalyst in respect to its space-time yield, specific activity, and/or its selectivity In U.S. Pat. Nos. 5,179,056; 5,189,004; and 5,342,987 by W. J. Barley it is reported that a shell impregnated catalysts of the Bissot type is improved in respect to its STY if it is essentially free of sodium; such as if it prepared from ingredients that are essentially free of sodium as per the '056 patent, or if its sodium content is removed by washing with water or an aqueous solution of a potassium promoter as in the '004 patent, or by washing the catalyst at an intermediate stage of its production with an ion exchange solution as in the '987 patent. In all of the above patents the exemplified catalyst are reduced with hydrazine solutions. U.S. Pat. No. 5,693,586 reports that a shell impregnated catalysts of the Bissot type which are made from reagents that are all potassium salt compounds are of an improved carbon dioxide selectivity. In this patent all example catalyst are reduced with ethylene at a temperature of 150° C.

Barley et al. in U.S. Pat. No. 5,274,181 reports that a shell impregnated catalysts of the Bissot type is improved in respect to its STY if it is prepared to have, at a Pd loading of 2.5 μL (0.33 wt %) to 6.1 g/L (1.05 wt %), a weight ratio of Au to Pd in the range of 0.6 to 1.25. All catalyst examples of this patent are reduced by reaction with a hydrazine solution.

U.S. Pat. No. 5,567,839 reports that a shell impregnated catalysts of the Bissot type is improved in respect to its STY if a barium salt rather than a sodium silicate is use to precipitate the Pd and Au compounds into the shell. All catalyst examples of this patent are reduced by reaction with a hydrazine solution.

The selectivity of a palladium-gold catalyst in vinyl acetate synthesis also is influenced by the extent and uniformity of the palladium metal and gold metal distribution on the exterior and/or interior surfaces of a porous catalyst support substrate, such as carbon dioxide selectivity and oxygen conversion in an ethylene, acetic acid and oxygen vapor phase reaction.

Attempts to provide a uniform distribution of the palladium and gold metals on the catalyst support has involved manipulation of the catalyst preparation steps and/or by using support substrates having various specified pore dimensions. Particularly useful improvements in preparing highly active catalysts for vinyl acetate production are disclosed in U.S. Pat. No. 5,314,858 and U.S. Pat. No. 5,332,710. These references describe process embodiments for improving palladium and gold distribution on a support by manipulating the precipitation step in which the water-soluble precious metal compounds are fixed to the support surface as water-insoluble compounds. In U.S. Pat. No. 5,314,858, fixing precious metals on the support is achieved utilizing two separate precipitation stages to avoid using large excesses of fixing agent. U.S. Pat. No. 5,332,710 describes fixing the precious metals by physically rotating an impregnated catalyst support while the impregnated support is immersed in a reaction solution at least during the initial precipitation period. The rotation immersion procedure yields catalysts in which the metals precipitated on the carrier are said to be more evenly distributed in a thin shell on the support surface. All catalyst examples of these patents are reduced with ethylene at a temperature of 150° C.

U.S. Pat. No. 6,420,308 by A. K. Khanmamedova (Khanmamedova'308) showed that the sequence of steps is critical. In Bissot'096 the catalyst was washed after reduction whereas in Khanmamedova'308 the catalyst was washed before reduction and obtained higher space time yield, and higher vinyl acetate selectivity.

Despite such improvements as have been made there is a continuing interest in the development of catalyst compositions that exhibit an even further improved combination of properties for the production of vinyl acetate.

SUMMARY OF THE INVENTION

This invention relates to a shell impregnated catalyst of Pd—Au, and methods for their production, which are effective for catalyzing the vapor phase reaction of ethylene with acetic acid and oxygen to produce vinyl acetate at high values for space-time yield, specific activity, and with a high selectivity for conversion of ethylene to vinyl acetate. This invention uses the same sequence of steps as in Khanmamedova but adds certain improvements:

1) palladium to gold weight ratio in the range from 2:8 to 8:2,
2) precipitating palladium and gold compounds to 70 to 100% of the total pore volume of the support particles,
3) a 1.1 to 2.2 molar excess of precipitating agent,
4) contact time with the precipitating agent for three hours up to seventy-two hours,
5) contact with the precipitating agent in light protected environment,
6) using a powdered precipitating agent,
7) washing the precipitated support with water at a temperature of from 50 to 80° C.,
8) reducing the catalyst precursor in nitrogen,
9) impregnating with potassium alkanoate in a solution of 5–12 wt. %,
10) final drying of the catalyst in nitrogen at 95° C. to 150° C. for one hour to twenty-four hours.

The shell impregnated catalyst of Pd—Au are produced on a silica support to have a Pd loading of 1.8 to about 7.2 g/L of catalyst and a Pd:Au weight ratio of 8:2 to 2:8 by impregnating the support with aqueous solutions of palladium and gold salts or acids, which preferably are high purity potassium tetrachlorpalladate (99.99%) and hydrogentetrachloraurate trihydrate (99.998%), and thereafter precipitating or "fixing", preferably in a light protected environment, water insoluble compounds of Pd and Au on the support surface by reaction for three to seventy-two hours of the impregnated support with solutions or powders of alkali metal metasilicates or alkali metal hydroxides or mixtures thereof as precipitating or "fixing" agents, preferably with a sodium metasilicate solution being used as a precipitating agent, to a volume corresponding to 70% to 100% of the total pore volume of the support particle in a quantity that exceeds the theoretical amount required to neutralize the Pd and Au salts to a 1.1 to 2.2 molar excess. The excess of fixing agent also depends on volume of fixing solution and acidity of support.

The impregnated support is then washed with deionized water at a temperature of 50° C. to 80° C. until the final decant is negative to a silver nitrate test, after which it is dried for water removal. The dried support with its surface precipitated compounds of Pd and Au is then reacted with ethylene, nitrogen or hydrogen at a temperature greater than 150° C. and for ethylene up to 310° C., for nitrogen up to 500° C. and for hydrogen up to 299° C., preferably for 10 minutes to one hour at a temperature of from 250° C. to 325° C. for ethylene, more preferably 250° C. to 310° C., from 300° to 450° C. for nitrogen and from 250° C. to 299° C. for hydrogen, until substantially all of its content of Pd and Au are reduced to their free metal state, after which the support is impregnated with potassium acetate to an extent of 5 to 12 weight percent of the weight of the reduced catalyst. Thereafter the catalyst is dried in air or in nitrogen at 90–150° C. for one to twenty four hours, preferably in nitrogen at 120° C. for one hour.

A catalyst as described above has a space-time yield (STY) and specific activity (SA) about 20–30% greater than an otherwise identical catalyst composition that is reduced with ethylene or hydrogen at 150° C. In a temperature range of 140° C. to 160° C. at a gas hourly space velocity of 4500/hr the catalyst will exhibit a vinyl acetate selectivity of 90% or greater when operated under reaction conditions that result in a STY of at least 600 gVA/L catalyst/hr. Further, such catalysts have a long operational life.

DETAILED DESCRIPTION OF INVENTION

This invention comprises a catalyst for the promotion of a gas phase reaction of an alkene, an alkanoic acid, and an oxygen-containing gas to produce an alkenyl alkanoate. The catalyst is particularly desirable for the gas phase reaction of an ethylene, an acetic acid, and an oxygen-containing gas to produce vinyl acetate.

In the catalyzed gas phase reaction process, ethylene reacts exothermically with acetic acid and oxygen in the vapor phase over a heterogeneous Pd—Au shelled catalysts, giving vinyl acetate and water:

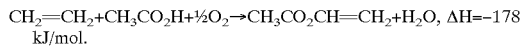

$$CH_2=CH_2+CH_3CO_2H+\tfrac{1}{2}O_2 \rightarrow CH_3CO_2CH=CH_2+H_2O, \Delta H=-178 \text{ kJ/mol.}$$

The vinyl acetate reaction process may typically operate at 140–180° C., 5–10 atmospheres (atm), and a gas hourly space velocity (GHSV) of ~4500 h⁻. This will give 8–10% ethylene and 15–40% acetic acid conversion. Oxygen conversion can be up to 90%, and the yields are up to 99% and 94% based on acetic acid and ethylene, respectively.

Reaction temperatures may be between 140° C. and 200° C. Generally the preferred reaction temperature range is 140° C. to 180° C. with 140–160° C. being most preferred. At temperatures below 140° C., the reaction rate is low and it is difficult to keep the acetic acid in the vapor phase.

Above 180° C., for a given catalyst, more and more of the ethylene and acetic acid feeds are converted to by products. The principal by product is carbon dioxide. Generally, the other by-products, acetaldehyde, and ethyl acetate are formed at about 1% or less.

Reaction pressures are between 70–200 psig. Typically, the pressure used in commercial plants is 100–150 psig. Higher pressures make it difficult to keep the acetic acid in the vapor phase whereas pressures lower than 70 psig too greatly reduce the STY of the reaction.

The total volume of reaction gases as a gas hourly space velocity (GHSV) is about 3000–5000 STP liter/liter of catalyst per hour. Higher GHSV values result in higher STY and SA values without significantly lowering the selective values for production of vinyl acetate. Therefore, higher GHSV values, such 4500, are preferred. The composition of the reaction gases in volume % is in the range of ethylene, 27–60%; inerts 15–55%; acetic acid 12–17% and oxygen 6–8%. The reaction is operated with a large excess of ethylene and acetic acid. The main reason for doing so is to avoid formation of potentially flammable/explosive mixtures. Oxygen levels above about 9% are not used in order to avoid explosive mixtures. The preferred ranges, respectively are ethylene 50–60%, inerts 20–50%, acetic acid 12–15%, and oxygen 6–7%. Commercially, oxygen is often used in place of air and the percentage of ethylene in the feed is raised.

The support particles used in the process of producing catalyst of this invention are solid particulate materials that are capable of being impregnated with palladium, gold and a potassium promoter and that are inert under the conditions used to produce alkenyl alkanoates, such as vinyl acetate. Illustrative of such support particles are particulate silica, alumina, and silica-aluminas. Silica is the preferred support. The support preferably has a surface area from 100 to 800 square meters per gram. Silica beads of an average diameter of 5 to 6 mm, a surface area of 150 to 200 square meters per gram and a pore volume of 0.6 to 0.7 ml/g, such as "KA-160" sold by Sud Chemie AG, is an example of a most preferred support material.

The aqueous solutions of water-soluble palladium and gold compounds used in the process of this invention may include aqueous solutions of any suitable palladium or gold compound such as palladium (II) chloride, alkali earth metal tetrachloropalladium (II), palladium (II) nitrate, palladium (II) sulfate, gold (III) chloride or auric (III) acid ($HAuCl_4$). However, compounds containing sodium are less preferred and the preferred compounds are potassium tetrachlorpalladate and hydrogentetrachloraurate. Then, for obtaining a high value for the space-time yield (STY) and specific activity (SA) of the catalyst it is preferred to utilize these preferred compounds in their high purity form, meaning 99.9+%purity, preferably 99.99%. Hence, it is preferred to use a potassium tetrachloropalladium of 99.99% purity and hydrogentetrachloraurate of 99.998% purity.

The quantity of Pd and Au compounds to be employed is such as to provide in the final catalyst a Pd loading of from about 1.8 g/L to about 7.2 g/L and a Au loading that places Au in the catalyst in a weight ratio to Pd in the Pd:Au range from 8:2 to 2:8, preferably 7:3 to 4:6, more preferably 6:4 to 5:5. Preferably the quantity of Pd loaded in the catalyst is such to provide the catalyst with a specific activity of greater than 200 g VA/g Pd/hr when operated under reaction conditions of 120 psig and within a temperature range of about 140° C. to about 160° C. that provide a STY of at least about 600 gVA/L cat/hr. The lower is the Pd loading that can be used to obtain the requisite STY values the higher will be the selectivity of conversion to VA, hence Pd loadings in a range of about 3.0 g/L to about 5.4 g/L are preferred.

The support is impregnated in a process designated as "rotation immersion to a point of incipient wetness." The volume of the impregnation solution preferably corresponds to from 70 to 100% (more preferably from 85 to 95%, most preferably about 90%) of the pore volume of the support. In this process, the catalyst support is immersed in the Pd—Au impregnation solution and tumbled or rotated therein during the initial stages of the impregnation of the support with the soluble precious metal compounds. The rotation or tumbling of the supports in the solution should proceed until all of the solution is absorbed which will depend on the volume of Pd—Au impregnating solution. Typically, for laboratory quantities, rotation is for at least 3 minutes and, preferably, for 3–15 minutes and more preferably 3–5 minutes. Excessive rotation can cause evaporation, loss of water and drying which can result in non-uniform distribution of palladium and gold, especially when the volume of the impregnation solution corresponds to 90% or less of the pore volume of the support.

Any type of rotation or tumbling equipment can be used as the exact apparatus utilized is not critical. However the extent of the rotating motion may be critical. The rotation should be fast enough so that all surfaces of the impregnated supports are evenly contacted with the impregnation solution as soon as possible. The rotation should not be so harsh that actual abrasion of the support particles takes place. Generally, the extent of rotation should be about 1 to 30 rpm and possibly even higher especially in the beginning of rotation depending upon the exact support utilized, the amount of support and the amount of precious metal to be impregnated into the support. The rpm to be used is variable and may also depend upon the apparatus utilized, the size and shape of the support, the type of support, and metal loading.

The precipitating agents used in the process of the present invention catalysts include sodium, lithium and potassium silicates, hydroxides and chlorides. It is preferred to use potassium chloride, sodium metasilicate, sodium hydroxide or potassium hydroxide as the precipitating agent. The precipitating agents are preferably employed in the form of aqueous solutions containing a 1.1 to 2.2 molar excess of the precipitating agents depending on support acidity and volume of used solution, preferably a 1.2 to 2.1 molar excess, more preferably a 1.5 molar excess. The volume of such solutions used is preferably just sufficient to cover the support particles. The impregnated support is immersed into the fixing solution and allowed to remain completely covered for three hours up to about 3 days (approximately 72 hours), preferably fifteen hours to 3 days, more preferably 1 day (approximately 24 hours) to 3 days, most preferably 3 days) at room temperature until a final pH value of 6.5–9.0 is attained. The exact quantity of alkali, time of fixing and final pH is dependent on the alkali type, the acidity of the support, and the quantities of precious metals used.

While the precipitating agent may be an aqueous solution, it may also be a powder used in a "dry fixing" technique to precipitate compounds of palladium and gold on the support surface. The powder may be added to the impregnated support beads or the impregnated support beads may be added to the powder. The solid—solid mixture may be rotated or agitated to uniformly mix the powder and the impregnated support beads in order to ensure that the precipitating agent is brought into contact with the water-soluble palladium and gold compounds so that water-insoluble palladium and gold compounds may be precipitated onto the support particles. The contact time may be the same as for the aqueous solution, i.e., three hours up to about 3 days (~72 hours), but preferably will be 12 to 36 hours, more preferably about 24 hours.

The reaction during the fixing step may be photosensitive. The source of gold, e.g., hydrogen tetrachloroaurate trihydrate, used in the catalyst synthesis may be sensitive to light and decompose with formation of separate phases. While the invention is not to be limited or restricted by theory, it is believed that the gold and palladium compounds are transformed to hydroxides of gold and palladium during the fixing step which, when reduced, result in palladium-gold interaction, with possible alloy formation. Gold hydroxides and palladium hydroxides separated on the surface of a support will be reduced with formation of inert gold metal and less active palladium metal. Exposure to light may decompose the gold and/or palladium compounds and may interfere with the formation of mixed hydroxides.

After fixation is completed the impregnated support beads are then removed from fixing solution and washed with deionized (D.I.) water at a temperature of 50 to 80° C., preferably 50 to 60° C. Further washing may then done in a batch or a continuous mode. Further washing at 50 to 80° C., preferably 50 to 60° C., should continue until the decant wash water content of chlorine ions is around 50 ppm, wherein the final decant gives a negative result to a silver nitrate test. Washing in water at a temperature above room temperature is believed not only to remove chlorine ions and sodium ions but also to remove amorphous silica particles from the pores.

After washing is complete the impregnated support beads are dried, such as at 90–150° C. in a forced air oven.

The reducing agent used in the process of this invention is ethylene, nitrogen or hydrogen to which the dried impregnated support are exposed while at a temperature greater than 150° C. and up to 310° C. for ethylene, up to 500° C. for nitrogen and up to 299° C. for hydrogen, preferably of or greater than 200° C. and more preferably to a temperature greater than 250° C. such as a range of 275° to 310° C. for ethylene, 300° to 450° C. for nitrogen and 275° C. to 299° C. for hydrogen, and most preferably at 300° C. for ethylene, 450° C. for nitrogen and 299° C. for hydrogen, for a time sufficient to complete the reduction of Pd and Au to their free metal state. Generally, the reduction is carried out for no longer than five hours, and preferably reduction in ethylene for less than one hour, preferably reduction in nitrogen for about one hour, and preferably reduction in hydrogen for about 10 to 30 minutes.

For purposes of their reduction the impregnated support beads may first be heated in a flow of gas, such as a nitrogen flow, from room temperature to 150° C. The impregnated support may then be held in the gas flow at 150° C. for 0.5–1 hour. Adsorbed water evolves during this heating period. The temperature may then be raised to 299–300° C., preferably increasing at 20–30°/min. Optionally, the impregnated support beads may be maintained at 299–300° C. for 10–30 minutes. Then the catalyst beads may be exposed to the reducing gas. If the reducing gas is ethylene or hydrogen, a volume of ethylene or hydrogen (1–5% by volume, preferably) may be introduced into the gas flow to form a reducing gas mixture.

For purpose of their reduction, dried impregnated beads may be directly placed into a heater at 300° C. with an ethylene-nitrogen gas flow mixture or at 299° C. with a hydrogen-nitrogen gas flow mixture or at 450° C. with a nitrogen gas flow. Dried beads should not be exposed to moisture before reduction. The reducing gas flow has to be sufficient to provide complete reduction of the catalyst metals and may be varied in contact time range.

After about 10–15 minutes to about 5 hours of reduction in the reducing gas or reducing gas mixture, the beads may then be cooled back to room temperature in nitrogen. Shorter reduction times yield catalysts of higher STY values; hence shorter reduction times of from about 15 minutes to about 0.5 hour are preferred.

The potassium promoters used in the process of this invention for producing the catalysts may include potassium alkanoates and any potassium compound that is converted to a potassium alkanoate during the alkenyl alkanoate-forming reaction (i.e., the reaction of ethylene, an alkanoic acid and an oxygen-containing gas in the presence of the catalyst to produce an alkenyl alkanoate). Potassium acetate is preferred as the promoter and is preferably added to the extent of about 5–12 wt. %, of the weight of the reduced catalyst, preferably 6–10 wt. %, more preferably 6–8 wt. %. The promoter is preferably applied in the form of aqueous solutions. It is preferred to accomplish placement of the promoter on the reduced impregnated support beads by the "rotation immersion to a point of incipient wetness" technique as previously described.

The catalyst is finally dried to remove water in air or nitrogen, preferably nitrogen. During this drying, the catalyst may be heated from room temperature to a temperature of 90–150° C., more preferably 95–120° C. Preferably, the temperature increase from room temperature to the final drying temperature is 20–30°/minute. The catalyst is dried for at least one hour and up to 24 hours at the final drying temperature. Preferably, the catalyst is dried in nitrogen at 120° C. for one hour.

EXAMPLES

Catalyst Preparation

Unless otherwise indicated, in all of the examples to follow the raw materials used for production of catalyst are as follows:

Support: KA-160; Gold: Hydrogen tetrachloroaurate (III) trihydrate, Palladium: Potassium or sodium tetrachloropalladate (II), 99.99%; Fixing agent: Sodium metasilicate anhydrous; Promoter: Potassium acetate; Water: Deionized water (D.I.), ~18 megohm-cm resistance; Reducing Agent: 5% ethylene in nitrogen or 5% hydrogen in nitrogen, as indicated.

Generally, the synthesis procedure for preparation of the catalysts of the present invention follows the procedure disclosed in copending U.S. application Ser. No. 09/612,159. Certain improvements and variations in the procedure disclosed in that application are illustrated by the examples below.

Catalyst Reactions

Unless otherwise indicated, in all of the examples to follow the reactor and catalysts conditions were as follows:

Reactor:

A micro reactor unit built by Zeton Altamira was used for screening catalysts and was designed for attended operations. Gases were fed through a Brooks mass flow meters and acetic acid was fed by an ISCO syringe pump. Controls were manually operated. The unit was interfaced with an on line GC.

A reactor tube of ¾ inch diameter was used so the catalyst pellets could be inserted. Catalyst loading was typically 2.5 grams along with 37.5 grams of 5-mm glass beads as a diluent. All catalysts consist of a commercial silica type support; KA-160 marketed by Sud Chemie. The active component is palladium. Generally another metal, gold, and a promoter, potassium acetate are added to the catalyst. The catalysts are of the shell type in which the metals are located within the outer 0.10–0.15 mm of the 5-mm diameter spheres.

Temperatures:

Reactions were carried out at three different temperatures ranging between 135 and 170° C. For some of the STY values herein reported a least squares Arrhenius curve was calculated based upon the data points and the 140° C., 150° C., and 160° C. values for STY were determined and are reported in the table of results below. Likewise the selectivity of conversion to vinyl acetate (VA) were measured at the three temperatures and a polynomial curve was calculated and the selectivity values at 140° C., 150° C., and 160° C. were determined and are reported in the tables of results below. Otherwise, the actual temperature, conversion and space time yield are reported. The principal by product was carbon dioxide. Generally, the other by products, acetaldehyde and ethyl acetate, were formed at about 1% or less.

Pressures:

Reaction pressures were either 120 psig or 50 psig as reported in the table of results below. Typically, pressure used in commercial plants is 100–150 psig. Some runs with the catalyst of this invention were conducted at a reaction pressure of 120 psig. High performing catalysts are better compared in the lab at 50 psig due to mass transport problems at 120 psig. Pressure was maintained at 50 psig for a latter series of runs. The STY of a catalyst at 50 psig of pressure was found to be about one half the value of that catalyst when run at 120 psig.

Flow Rates:

The total volume (GHSV) of reaction gases was maintained at 4,500 STP liter/liter of catalyst per hour. Initial volume % used in these examples are 55% $C_2H_4$, 26.0% He, 12.5% acetic acid and 6.5% $O_2$. Oxygen in these examples is introduced as a 20% oxygen-80% helium blend. For the evaluation of 2.5 grams of whole beads, the flow rates were: ethylene 179 standard cubic centimeters (sccm), 20% $O_2$ 106 sccm, and acetic acid 40.75 sccm. Gas flow rates were controlled and measured by Brooks mass flow controllers with ranges of 0–500 sccm.

Acetic acid was fed as a liquid and flow rate was controlled by an ISCO pump that can give a minimum flow rate of 0.1 μl/min (liquid). The acetic acid liquid was vaporized by introducing it into a mixing tee at 150° C. along with the ethylene and $O_2$/He. The acetic acid (vapor) and other gases were then mixed in a static in line mixer before entering the reactor.

Flammability:

Flammability limits of the ethylene and oxygen mixture depend on temperature, pressure, and composition. It is shifted by additional components, such as acetic acid, and helium. In general, the oxygen concentration at the entry to the reactor is ≦9 vol. %, based on acetic acid free mixture. A PLC computer utilizing electrical output from the mass flow meters was used to prevent the formation of flammable ethylene oxygen mixtures.

Palladium-Gold Weight Ratio

Comparative Example 1A

Pd:Au=9:1

1. Impregnation Step.

A solution of 0.03240 g of $HAuCl_4.3H_2O$ and 0.51845 g of $K_2PdCl_4$ in 7.83 ml of DI water was used to impregnate 15 g of KA-160 at room temperature (R.T.) by an incipient wetness technique. The KA-160 was placed in a 0.5 liter round bottom flask. After pouring the solution over the KA-160, the flask was connected to a rotary evaporator. The flask was then rotated for 1–10 minutes until all the solution was adsorbed by the support.

2. Fixing Step.

0.32087 g of $Na_2SiO_3$ was dissolved in 13.5 ml of D.I. water. The impregnated support from step 1 was reacted with the fixing solution by pouring the fixing solution over the beads in a flask. The flask was rotated for 10 minutes and the sample was then transferred into a cabinet without light. The fixing reaction was allowed to proceed for overnight (15–18) hours at room temperature.

3. Washing Step.

The beads were then removed from fixing solution and separately immersed into 1 L of water at 50° C. A magnetic stirrer was applied during the wash. The wash water was decanted the next day and replaced with another 1 L portion of water. The washing/decanting procedure was carried out a total of 2–5 times to decrease content of chlorine ions to around 50 ppm, wherein the final decant gives a negative result to a silver nitrate test.

4. Drying Step.

The impregnated supports were then dried for fifteen hours at 95° C. in a forced air oven.

5. Reduction Step.

The reduction procedure was carried out in a glass or quartz tube heated with a tube furnace. The impregnated supports were heated in a nitrogen flow (rate 300–330 ml/min) from room temperature to 150° C. for one hour. The beads were further heated in nitrogen flow to 300° C. for 0.5 hour. Adsorbed water evolved during this heating period. Then the nitrogen flow was maintained and a 5% volume of ethylene in nitrogen mixture was introduced at a flow of 300–330 ml/min. After 5 hours of reduction at 300° C., the ethylene in the nitrogen mixture was turned off leaving a pure nitrogen flow. The beads were then cooled to room temperature under nitrogen.

6. Promoting Step.

Reduced impregnated support was promoted with 7 wt. % of potassium acetate by incipient wetness technique. Beads were placed into a flask.

7. Final Drying Step.

The catalyst was placed in an oven at room temperature. The temperature was increased to 120° C. The catalyst was dried at 120° C. for one hour in a nitrogen flow.

Example 1

Pd:Au=8:2

The procedure of the Example 1A was followed except:

1. Impregnation Step.

0.064807 g of $HAuCl_4.3H_2O$ 0.460843 g of $K_2PdCl_4$

2. Fixing Step.

0.31869 g of $Na_2SiO_3$

Example 2

Pd:Au=7:3
The procedure of the Example 1A was followed except:
1. Impregnation Step.
   0.09721 g of $HAuCl_4 \cdot 3H_2O$
   0.40322 g of $K_2PdCl_4$
2. Fixing Step.
   0.3165 g of $Na_2SiO_3$

Example 3

Pd:Au=6:4
The procedure of Example 1A was followed except:
1. Impregnation Step
   0.1296 g of $HAuCl_4 \cdot 3H_2O$
   0.3456 g of $K_2PdCl_4$
   7.56 g $H_2O$
   15 g KA-160
2. Fixing Step.
   0.31425 g of $Na_2SiO_3$
   13.03 mL $H_2O$

Example 4

Pd:Au=5.5:4.5
The procedure of Example 1A was followed except:
1. Impregnation Step.
   0.1713 g of $HAuCl_4 \cdot 3H_2O$
   0.3156 g of $K_2PdCl_4$
   7.57 g $H_2O$
   14.9785 g KA-160
2. Fixing Step.
   0.33675 g of $Na_2SiO_3$
   13.03 mL $H_2O$

Example 5

Pd:Au=5:5
The procedure of the Example 1A was followed except:
1. Impregnation Step.
   0.1620 g of $HAuCl_4 \cdot 3H_2O$
   0.2880 g of $K_2PdCl_4$
2. Fixing Step.
   0.3121 g of $Na_2SiO_3$

Example 6

Pd:Au=4:6
The procedure of the Example 1A was followed except:
1. Impregnation Step.
   0.19442 g of $HAuCl_4 \cdot 3H_2O$
   0.23042 g of $K_2PdCl_4$
2. Fixing Step.
   0.309957 g of $Na_2SiO_3$

Example 7

Pd:Au=2:8
The procedure of the Example 1A was followed except:
1. Impregnation Step.
   0.259228 g of $HAuCl_4 \cdot 3H_2O$
   0.115210 g of $K_2PdCl_4$
2. Fixing Step.
   0.305599 g of $Na_2SiO_3$

TABLE 1

Effect of Palladium to Gold Weight Ratio on VA Selectivity and Space Time Yield

| Example # | Reaction Temp. °C. | VA Selectivity (%) | Space Time Yield (50 psig) |
|---|---|---|---|
| Comparative Example 1A (9:1) | 138.0 | 92.2 | 241.5 |
| | 138.0 | 92.3 | 237.3 |
| | 138.0 | 92.5 | 231.0 |
| | 148.0 | 89.8 | 302.7 |
| | 148.0 | 90.1 | 292.6 |
| | 147.5 | 90.4 | 276.9 |
| | 158.0 | 86.0 | 364.0 |
| | 159.0 | 86.0 | 359.5 |
| | 159.0 | 86.3 | 351.8 |
| Example 1 (8:2) | 138.0 | 94.1 | 267.3 |
| | 139.0 | 94.3 | 275.8 |
| | 139.0 | 94.2 | 279.5 |
| | 149.0 | 92.4 | 396.5 |
| | 149.0 | 92.3 | 401.8 |
| | 149.5 | 92.4 | 402.1 |
| | 163.0 | 88.1 | 541.1 |
| | 164.0 | 88.0 | 546.7 |
| | 163.0 | 87.8 | 548.3 |
| | 164.0 | 88.2 | 542.0 |
| | 163.0 | 88.4 | 542.8 |
| Example 2 (7:3) | 139.0 | 94.1 | 315.1 |
| | 140.0 | 94.2 | 332.7 |
| | 140.0 | 94.3 | 344.7 |
| | 149.0 | 92.6 | 453.9 |
| | 149.0 | 92.4 | 455.8 |
| | 149.0 | 92.7 | 455.3 |
| | 161.5 | 89.2 | 581.4 |
| | 161.5 | 89.0 | 589.2 |
| | 162.0 | 89.1 | 587.8 |
| Example 3 (6:4) | 140.0 | 94.7 | 305.1 |
| | 140.0 | 94.6 | 342.0 |
| | 141.5 | 94.5 | 350.0 |
| | 148.0 | 93.2 | 437.5 |
| | 150.0 | 93.0 | 450.5 |
| | 151.0 | 92.9 | 465.7 |
| | 151.0 | 93.1 | 452.8 |
| | 159.0 | 90.6 | 540.5 |
| | 160.0 | 90.4 | 544.8 |
| | 160.0 | 90.3 | 544.4 |
| Example 4 (5.5:4.5) | 138.0 | 94.8 | 319.2 |
| | 139.0 | 94.9 | 323.5 |
| | 139.0 | 94.7 | 326.6 |
| | 148.0 | 93.4 | 423.7 |
| | 149.0 | 93.4 | 424.8 |
| | 149.0 | 93.4 | 425.7 |
| | 158.0 | 91.2 | 523.1 |
| | 158.0 | 91.0 | 524.9 |
| | 158.0 | 91.1 | 528.8 |
| Example 5 (5:5) | 138.0 | 95.0 | 266.0 |
| | 139.0 | 95.0 | 274.7 |
| | 139.0 | 95.0 | 277.1 |
| | 148.0 | 93.9 | 370.8 |
| | 148.0 | 94.0 | 373.8 |
| | 148.0 | 93.9 | 373.8 |
| | 158.0 | 91.8 | 480.5 |
| | 159.0 | 91.7 | 485.3 |
| | 159.0 | 91.8 | 472.3 |
| Example 6 (4:6) | 138.0 | 95.4 | 226.1 |
| | 138.0 | 95.4 | 234.0 |
| | 138.0 | 95.4 | 238.0 |
| | 147.5 | 94.5 | 314.5 |
| | 147.5 | 94.6 | 311.1 |
| | 147.0 | 94.6 | 312.1 |
| | 158.0 | 92.5 | 401.6 |
| | 158.0 | 92.4 | 406.0 |
| | 158.0 | 92.4 | 403.6 |

TABLE 1-continued

Effect of Palladium to Gold Weight Ratio on VA Selectivity and Space Time Yield

| Example # | Reaction Temp. ° C. | VA Selectivity (%) | Space Time Yield (50 psig) |
|---|---|---|---|
| Example 7 | 138.0 | 95.1 | 123.7 |
| (2:8) | 138.0 | 94.9 | 130.0 |
|  | 138.0 | 95.0 | 132.6 |
|  | 147.5 | 94.2 | 170.5 |
|  | 147.5 | 94.0 | 165.1 |
|  | 147.0 | 94.1 | 164.3 |
|  | 158.0 | 92.4 | 208.4 |
|  | 158.0 | 92.6 | 209.2 |
|  | 158.0 | 92.4 | 209.1 |

The catalysts were evaluated in the reactor in the conditions as described above. The results for VA selectivity and space time yield are shown in Table 1. The catalysts of Examples 3–7 (6:4, 5.5:4.5, 5:5, 4:6, 2:8) had better selectivity than the catalysts of Comparative Example 1A and Examples 1–2 (9:1, 8:2, 7:3). This data illustrates the advantages of preparing a catalyst having a Pd:Au weight ratio in the range from about 6:4 to about 2:8. The catalysts of Examples 1–5 (8:2, 7:3, 6:4, 5.5:4.5, 5:5) had better space time yield than the catalysts of Comparative Example 1A and Examples 6–7 (9:1, 4:6, 2:8). This data illustrates the advantages of preparing a catalyst having a Pd:Au weight ratio in the range from about 8:2 to about 5:5. A catalyst having a Pd:Au weight ratio in the range from about 8:2 to about 2:8, preferably 7:3 to about 4:6, more preferably 6:4 to 5:5 which appears to have the optimum performance of both selectivity and space time yield.

LIGHT PROTECTION

Example 9 and Comparative Example 9A

1. Impregnation Step.

A solution of 0.2284 g of $HAuCl_4 \cdot 3H_2O$ and 0.4208 g of $K_2PdCl_4$ in 9.28 ml of DI water was used to impregnate 20 g of KA-160 at room temperature (R.T.) by an incipient wetness technique. The KA-160 was placed in a 0.5 liter round bottom flask. After pouring the solution over the KA-160, the flask was connected to a rotary evaporator. The flask was then rotated for 10 minutes until all the solution was +adsorbed by the support. After this, rotation was stopped and the impregnated support was left undisturbed for at least 1 hour. During that time the flask with impregnated support was stoppered to prevent solution evaporation from the surface of support.

2. Fixing Step.

Example 9: 0.44832 g of $Na_2SiO_3$ was dissolved in 20 ml of D.I. water. Half of the impregnated support from step 1 was reacted with 10 ml of fixing solution by pouring the fixing solution over the beads in a flask covered with aluminum foil. The fixing solution barely covered the beads. The covered flask was rotated for 10 minutes and the sample was then transferred into a beaker covered with aluminum foil and sealed. The beaker was placed in a cabinet without light. The fixing reaction was allowed to proceed for 1 day (~24 hours) at room temperature.

Example 9A The other half of the impregnated support from step 1 was reacted with 10 ml of fixing solution by pouring the fixing solution over the beads. The fixing solution barely covered the beads. In room light, the flask was rotated for 10 minutes and the sample was then transferred into a beaker covered with glass. The covered beaker was placed under a 100 watt bulb. The fixing reaction was allowed to proceed for 1 day (~24 hours) at room temperature.

3. Washing Step.

The beads of both Example 9 and Example 9A were then removed from fixing solution and separately immersed into 0.5 L of water at 45–50° C. A magnetic stirrer was applied during the wash. The wash water was decanted the next day and replaced with another 0.5 L portion of water. The washing/decanting procedure was carried out a total of 5 times (the last time using 1 L of water) for both Example 9 and Example 9A to decrease content of chlorine ions to around 50 ppm, wherein the final decant gives a negative result to a silver nitrate test.

4. Drying Step.

The impregnated supports of both Example 9 and Example 9A were then dried for fifteen hours at 95° C. in a forced air oven.

5. Reduction Step.

The reduction procedure was carried out in a glass or quartz tube heated with a tube furnace separately for Example 9 and Example 9A. The impregnated supports were heated in a nitrogen flow (rate 300–330 ml/min) from room temperature to 150° C. for one hour. The beads were further heated in nitrogen flow to 300° C. for 0.5 hour. Adsorbed water evolved during this heating period. Then the nitrogen flow was maintained and a 5% volume of ethylene in nitrogen mixture was introduced at a flow of 300–330 ml/min. After 5 hours of reduction at 300° C., the ethylene in the nitrogen mixture was turned off leaving a pure nitrogen flow. The beads were then cooled to room temperature under nitrogen.

6. Promoting Step.

Reduced impregnated supports of Example 9 and Example 9A were separately promoted with 7 wt. % of potassium acetate (KOAc) by incipient wetness technique. Beads were placed into a flask.

7. Final Drying Step.

The catalysts of Example 9 and Example 9A were separately place in an over at room temperature. The temperature was increased to 120° C. The catalysts were dried at 120° C. for one hour in a nitrogen flow.

TABLE 2

Comparison of Light-Protected and Light Exposed Catalysts

| Example # | Reaction Temperature (° C.) | VA Selectivity (%) | Space Time Yield (50 psig) |
|---|---|---|---|
| Example 9 | 140 | 94.4 | 250 |
| (Light | 150 | 92.6 | 370 |
| Protection) | 160 | 90.4 | 475 |
| Comparative | 140 | 93.8 | 220 |
| Example 9A | 150 | 92.6 | 320 |
| (Light Exposure) | 160 | 90.4 | 425 |

The catalysts of Example 9 (with light protection) and Comparative Example 9a (exposed to light) were evaluated in the reactor in the conditions as described above. The results for VA selectivity and space time yield are shown in Table 1. The data illustrates the advantages of preparing a catalyst in an environment protected from light at the fixing step. The catalyst of Example 9 had as good or better VA selectivity and consistently better space time yield as the catalyst of Comparative Example 9A.

Examples 10–14 and Comparative Examples 10A and 10B

Pore Volume Fill

Example 10

100% Pore Filling

1. Impregnation Step

A solution of 0.1713 g of $HAuCl_4 \cdot 3H_2O$ and 0.3156 g of $K_2PdCl_4$ in 8.7 mL of DI water was used to impregnate 14.9978 g of KA-160 at room temperature by an incipient wetness technique. The KA-160 was placed in a round bottom flask. After pouring the solution over the KA-160, the flask was connected to a rotary evaporator. The flask was rotated for 5 minutes. After the rotation was stopped, the impregnated support was let stand for one hour.

2. Fixing Step

The fixing solution of $Na_2SiO_3$ (0.4035 g in 30 mL of water) was poured over the beads. The flask was rotated for 10 minutes. The solution was allowed to stand for 24 hours at room temperature.

3. Washing Step

The beads were washed by immersing them in 1 L of D.I. water at 50° C. The water layer above the bead was gently stirred for approximately 24 hours. The wash water was decanted and replaced with another 1 L of D.I. water. This procedure was repeated for a total of three washes.

4. Reduction Step

Reduction was carried out in a glass or quartz tube heated with a tube furnace. The beads were heated in nitrogen at 150° C. for one hour and then heated further by a nitrogen flow for 30–40 minutes at 300° C. and reduced at that temperature for one hour in an ethylene flow. The beads were cooled to room temperature in nitrogen.

5. Promoting Step

The reduced sample was promoted with 7 wt. % potassium acetate by incipient wetness.

6. Final Drying

The sample was placed in an oven at room temperature. The temperature was increased to 120° C. The catalyst was dried with nitrogen at 120° C. for one hour. The VA selectivity and space time yield are shown in Table 3.

Example 11

95% Pore Filling

The procedure of Example 10 was followed except:
0.2104 g $K_2PdCl_4$
0.1142 g $HAuCl_4 \cdot 3H_2O$
5.51 mL of D.I. water
9.98 g of KA-160
The impregnated support was not allowed to stand before the fixing step 0.269 g of $Na_2SiO_3$ in 30 mL of water
After washing the beads were dried in air for fifteen hours at 95° C.
The VA selectivity and space time yield are shown in Table 3.

Example 12

90% Pore Filling (A1-2-26-2N₂)

The procedure of Example 10 was followed except:
0.4205 g $K_2PdCl_4$
0.2290 g $HAuCl_4 \cdot 3H_2O$
10.672 mL of D.I. water
20 g of KA-160
The VA selectivity and space time yield are shown in Table 3.

Example 13

85% Pore Filling

The procedure of Example 10 was followed except:
0.2104 g $K_2PdCl_4$
0.1142 g $HAuCl_4 3H2O$
4.93 mL of D.I. water
9.96 g of KA-160
0.269 g of $Na_2SiO_3$ in 20 mL of water
After washing the beads were dried in air for fifteen hours at 95° C.
The VA selectivity and space time yield are shown in Table 3.

Example 14

80% Pore Filling

The procedure of Example 10 was followed except:
0.2104 g $K_2PdCl_4$
0.1142 g $HAuCl_4 3H_2O$
4.64 mL of D.I. water
9.99 g of KA-160
0.269 g of $Na_2SiO_3$ in 20 mL of water
After washing the beads were dried in air for fifteen hours at 95° C.
The VA selectivity and space time yield are shown in Table 3.

Example 15

70% Pore Filling

The procedure of Example 10 was followed except:
0.2104 g $K_2PdCl_4$
0.1142 g $HAuCl_4 3H2O$
4.06 mL of D.I. water
10.0252 g of KA-160
20 mL of a solution prepared from 1.345 g of $Na_2SiO_3$ in 100 mL of water
The beads were washed with D.I. Water at 45–50° C.
After washing the beads were dried in air for fifteen hours at 95° C.
The VA selectivity and space time yield are shown in Table 3.

Comparative Example 10A

60% Pore Filling

The procedure of Example 10 was followed except:
0.2104 g $K_2PdCl_4$
0.1142 g $HAuCl_4 3H2O$
3.48 mL of D.I. water
10 g ofKA-160
20 mL of a solution prepared from 1.345 g of $Na_2SiO_3$ in 100 mL of water
The beads were washed with D.I. Water at 45–50° C.
After washing the beads were dried in air for fifteen hours at 95° C.
The VA selectivity and space time yield are shown in Table 3.

TABLE 3

Variation in support pore volume filling with Pd—Au solution

| Example # | Pd Wt. % Calculated (Actual) | Au Wt. % Calculated (Actual) | Reaction Temp. °C. | VA Selectivity (%) | Space Time Yield (50 psig) | Expected Space Time Yield @ 120 psig |
|---|---|---|---|---|---|---|
| Example 10 (100%) | 0.63 (0.65) | 0.52 (0.26) | 140 | 93.0 | 230 | 460 |
|  |  |  | 150 | 91.0 | 325 | 650 |
|  |  |  | 160 | 88.2 | 410 | 820 |
| Example 11 (95%) | 0.63 (NA) | 0.52 (NA) | 140 | 93.8 | 265 | 530 |
|  |  |  | 150 | 91.9 | 370 | 740 |
|  |  |  | 160 | 89.1 | 480 | 960 |
| Example 12 (90%) | 0.63 (0.63) | 0.52 (0.28) | 140 | 93.0 | 290 | 580 |
|  |  |  | 150 | 91.3 | 400 | 800 |
|  |  |  | 160 | 88.2 | 505 | 1010 |
| Example 13 (85%) | 0.63 (NA) | 0.52 (NA) | 140 | 94.1 | 260 | 520 |
|  |  |  | 150 | 92.4 | 380 | 760 |
|  |  |  | 160 | 89.6 | 490 | 980 |
| Example 14 (80%) | 0.63 (0.63) | 0.52 (0.23) | 140 | 93.6 | 235 | 470 |
|  |  |  | 150 | 91.8 | 340 | 680 |
|  |  |  | 160 | 89.2 | 450 | 900 |
| Example 15 (70%) | 0.63 (NA) | 0.52 (NA) | 140 | 93.8 | 260 | 520 |
|  |  |  | 150 | 91.6 | 360 | 720 |
|  |  |  | 160 | 88.4 | 460 | 920 |
| Comparative Example 10A (60%) | 0.63 (0.67)* | 0.52 (0.25)* | 140 | 93.2 | 170 | 340 |
|  |  |  | 150 | 91.6 | 260 | 520 |
|  |  |  | 160 | 88.8 | 360 | 720 |

The catalysts were evaluated in the reactor in the conditions as described above. The results for VA selectivity and space time yield are shown in Table 3. The data illustrates the advantages of a catalyst having 70 to 100% of the pore volume filled with the impregnation solution. The catalyst of Examples 10–15 have as good or better VA selectivity and consistently better space time yield as the catalysts of Comparative Example 10A. A more preferred range of pore volume is 85 to 95% and most preferred is a pore volume of about 90%.

Examples 16–18 and Comparative Example 16A
Amount of Fixing Agent

Example 16

1. Impregnation Step.

A solution of 0.571 g of $HAuCl_4 \cdot 3H_2O$ and 1.051 g of $K_2PdCl_4$ in 29.6 ml of DI water was used to impregnate 50 g of KA-160 at room temperature (R.T.) by an incipient wetness technique. The KA-160 was poured over the Pd—Au solution in a half-liter round bottom flask. After pouring the solution over the KA-160, the flask was connected to a rotary evaporator. The flask was then rotated very slowly for one hour. After this, rotation was stopped and the impregnated support was left undisturbed for 1 hour. During that time the flask with impregnated support was stoppered to prevent solution evaporation from the surface of support. Then sample was divided in 5 equal parts for synthesis with different fixing steps.

2. Fixing Step.

0.2241 g of $Na_2SiO_3$ was dissolved in 7.5 ml of D.I. water. The impregnated support from step 1 was reacted with the fixing solution by rapidly pouring the fixing solution over the beads. The fixing solution completely covered the beads. The fixing reaction was allowed to proceed for 1 day (~24 hours) at room temperature.

3. Washing Step.

The beads were then removed from fixing solution and immersed into 1L of water at 50° C. The water layer above the beads was gently stirred overnight. The wash water was decanted the next day and replaced with another 1 L portion of water. The washing/decanting procedure was carried out a total of 3 times to decrease content of chlorine ions to around 50 ppm, wherein the final decant gives a negative result to a silver nitrate test.

4. Drying Step.

The impregnated support was then dried for 24 hours at 95° C. in air.

5. Reduction Step.

The reduction procedure was carried out in a glass or quartz tube heated with a tube furnace. The impregnated support was heated in a nitrogen flow (rate 300–330 ml/min) from room temperature to 150° C. for one hour. The beads were then further heated in a nitrogen flow to 300° C. maintained at that temperature for a half hour. Adsorbed water evolved during this heating period. Then the nitrogen flow was maintained and a 5% volume of ethylene in nitrogen mixture was introduced at a flow of 300–330 ml/min. After 1 hour of reduction in nitrogen mixture at 300° C., the ethylene was turned off leaving the pure nitrogen flow. The beads were then cooled to room temperature under nitrogen.

6. Promoting Step.

Reduced impregnated support was promoted with 7 wt. % of potassium acetate (KOAc) by incipient wetness technique. Beads were placed into a flask.

7. Final Drying Step

The catalyst was dried overnight at room temperature and then placed in an oven at room temperature. The temperature was increased to 120° C. The catalyst was dried at 120C for one hour in a nitrogen flow.

Examples 17 and 18 and Comparative Example 16A

The same procedure for Example 16 was followed except for the fixing step in which the following were used:

| | | |
|---|---|---|
| $Na_2SiO_3$: 0.1943 g | D.I. water: 7.5 ml | |
| $Na_2SiO_3$: 0.1644 g | D.I. water: 7.5 mL | |
| $Na_2SiO_3$: 0.1195 g | D.I. water: 7.5 mL | |

TABLE 4

Amount of Fixing Agent (0.8–1.5 Molar Excess)

| Example # | Reaction Temp. ° C. | VA Selectivity (%) | Space Time Yield (50 psig) |
|---|---|---|---|
| Example 16 | 140 | 93.3 | 310 |
| (1.5 XS) | 150 | 91.0 | 400 |
| | 160 | 88.0 | 490 |
| Example 17 | 140 | 94.4 | 250 |
| (1.3 XS) | 150 | 93.2 | 370 |
| | 160 | 91.0 | 440 |
| Example 18 | 140 | 94.6 | 240 |
| (1.1 XS) | 150 | 93.3 | 340 |
| | 160 | 91.2 | 440 |
| Comparative | 140 | 94.6 | 150 |
| Example 16A | 150 | 93.3 | 210 |
| (0.8 XS) | 160 | 91.0 | 300 |

The catalysts were evaluated in the reactor in the conditions as described above. The results for VA selectivity and space time yield are shown in Table 4. The data illustrates the advantages of a catalyst having been synthesized with a molar excess of precipitating or fixing agent of at least 1.1. The catalysts of Examples 16–18 had consistently better space time yield than the catalyst of Comparative Example 16A.

Examples 19 and 20 and Comparative Examples 19A–19C

1. Impregnation Step.

A solution of 0.572 g of $HAuCl_4 \cdot 3H_2O$ and 1.052 g of $K_2PdCl_4$ in 29.375 ml of DI water was used to impregnate 50 g of KA-160 at room temperature (R.T.) by an incipient wetness technique. The KA-160 was poured over the Pd—Au solution in a half-liter round bottom flask. After pouring the solution over the KA-160, the flask was connected to a rotary evaporator. The flask was then rotated for one hour. After this, rotation was stopped and the impregnated support was left undisturbed for at least 1 hour. During that time the flask with impregnated support was stoppered to prevent solution evaporation from the surface of support.

2. Fixing Step.

0.30398 g of $Na_2SiO_3$ was dissolved in 8.325 ml of D.I. water. One-fifth of the impregnated support from step 1 was reacted with the fixing solution by rapidly pouring the fixing solution over the beads. The fixing solution completely covered the beads. Final pH was 8.62. The fixing reaction was allowed to proceed for 1 day (~24 hours) at room temperature. This procedure was repeated for the following:

| | | |
|---|---|---|
| $Na_2SiO_3$: 0.32944 g | D.I. water: 8.325 mL | Final pH: 8.99 |
| $Na_2SiO_3$: 0.35939 g | D.I. water: 8.325 mL | Final pH: 9.04 |
| $Na_2SiO_3$: 0.38933 g | D.I. water: 8.325 mL | Final pH: 9.32 |
| $Na_2SiO_3$: 0.41929 g | D.I. water: 8.325 mL | Final pH: 9.45 |

3. Washing Step.

For Examples 19 and 20, the beads were then removed from fixing solution and Immersed into 0.5 L of water at room temperature. The water layer above the beads was gently stirred overnight. The wash water was decanted the next day and replaced with another 0.5 L portion of water. This washing/decanting procedure was carried out a total of three times and then repeated twice with 1L of water at 50° C. to decrease content of chlorine ions to around 50 ppm, wherein the final decant gives a negative result to a silver nitrate test.

For Comparative Example 19A, the beads were then removed from fixing solution and immersed into 225 mL of water at room temperature. The water layer above the beads was gently stirred overnight. The wash water was decanted the next day and replaced with another 225 mL portion of water. This washing/decanting procedure was carried out a total of three times, repeated with 1 L of water at room temperature, repeated with 2 L of water at 50° C. to decrease content of chlorine ions to around 50 ppm, wherein the final decant gives a negative result to a silver nitrate test.

For Comparative Examples 19B and 19C, the beads were then removed from fixing solution and immersed into 225 mL of water at room temperature. The water layer above the beads was gently stirred overnight. The wash water was decanted the next day and replaced with another 225 mL portion of water. This washing/decanting procedure was carried out a total of three times, repeated with 0.5 L of water at room temperature, repeated three times with 500 mL of water at 50° C. and repeated twice with 1 L of water at 50° C. to decrease content of chlorine ions to around 50 ppm, wherein the final decant gives a negative result to a silver nitrate test.

4. Drying Step.

For Examples 19 and 20 and Comparative Example 19A, the impregnated supports were then dried for 9 hours in air at 95° C.

For Comparative Examples 19B and 19C, the impregnated supports were then dried for 16 hours in air at 95° C.

5. Reduction Step.

The reduction procedure was carried out in a glass or quartz tube heated with a tube furnace. The impregnated supports were heated in a nitrogen flow (rate 300–330 ml/min) from room temperature to 150° C. for a half hour. The beads were then further heated in a nitrogen flow to 300° C. for a half hour. Adsorbed water evolved during this heating period. Then the nitrogen flow was maintained and a 5% volume of ethylene in nitrogen mixture was introduced at a flow of 300–330 ml/min. After 1 hour of reduction in nitrogen mixture at 300° C., the ethylene was turned off leaving the pure nitrogen flow. The beads were then cooled to room temperature under nitrogen.

6. Promoting Step.

Reduced impregnated supports were promoted with 6–7 wt. % of potassium acetate (KOAc) by incipient wetness technique. Beads were placed into a flask.

7. Final Drying Step.

For Example 19 and Comparative Examples 19B and 19C, each catalyst was separately placed in an oven at room temperature. The temperature was increased to 95° C. The catalyst was dried at 95° C. for sixteen hours in air.

For Example 20 and Comparative Example 19A, each catalyst was separately placed in an oven at room temperature. The temperature was increased to 75° C. The catalyst was dried at 75° C. for sixteen hours in air.

TABLE 5

Amount of Fixing Agent (2.0–2.8 Molar Excess)

| Example # | Pd Wt. % Calculated (Actual) | Au Wt. % Calculated (Actual) | Reaction Temp. °C. | VA Selectivity (%) | Space Time Yield (50 psig) | Expected Space Time Yield @ 120 psig |
|---|---|---|---|---|---|---|
| Example 19 (2.0 XS) | 0.63 (0.59) | 0.52 (0.28) | 140 | 92.4 | 260 | 520 |
|  |  |  | 150 | 90.5 | 340 | 680 |
|  |  |  | 160 | 87.1 | 430 | 860 |
| Example 20 (2.2 XS) | 0.63 (NA) | 0.52 (NA) | 140 | 92.3 | 260 | 520 |
|  |  |  | 150 | 90.1 | 345 | 690 |
|  |  |  | 160 | 86.6 | 420 | 840 |
| Comparative Example 19A (2.4 XS) | 0.63 (0.59) | 0.52 (0.26) | 140 | 92.2 | 240 | 480 |
|  |  |  | 150 | 89.7 | 310 | 620 |
|  |  |  | 160 | 86.2 | 370 | 740 |
| Comparative Example 19B (2.6 XS) | 0.63 (0.58) | 0.52 (0.26) | 140 | 92.0 | 220 | 440 |
|  |  |  | 150 | 89.8 | 280 | 560 |
|  |  |  | 160 | 86.3 | 395 | 790 |
| Comparative Example 19C (2.8 XS) | 0.63 (0.59) | 0.52 (0.25) | 140 | 91.7 | 215 | 430 |
|  |  |  | 150 | 89.4 | 280 | 560 |
|  |  |  | 160 | 85.4 | 350 | 700 |

The catalysts were evaluated in the reactor in the conditions as described above. The results for VA selectivity and space time yield are shown in Table 5. The data illustrates the advantages of a catalyst having been synthesized with a molar excess of precipitating or fixing agent of not more than 2.2. The catalyst of Examples 19 and 20 have as good or better VA selectivity and consistently better space time yield as the catalysts of Comparative Examples 19A–19C.

Examples 21–25

1. Impregnation Step.

A solution of 0.571 g of $HAuCl_4 \cdot 3H_2O$ and 1.052 g of $K_2PdCl_4$ in 26.1 ml of DI water was used to impregnate 50 g of KA-160 at room temperature (R.T.) by an incipient wetness technique. The KA-160 was placed in a one-liter round bottom flask. After pouring the solution over the KA-160, the flask was connected to a rotary evaporator. The flask was then rotated for 10 minutes until all the solution was adsorbed by the support. There was 77.7350 g of the impregnated support which was divided into five equal parts. Fixing started within five minutes.

2. Fixing Step.

0.3143 g of $Na_2SiO_3$ was dissolved in 9 ml of D.I. water. 15.50 g of the impregnated support from step 1 was reacted with the fixing solution by pouring the fixing solution over the beads. The volume of the solution was about half of the bead volume. The mixture was rotated for 5 minutes and then placed in a beaker and sealed. The fixing reaction was allowed to proceed for 1 day (~24 hours) at room temperature. This procedure was repeated for the following:

| | |
|---|---|
| $Na_2SiO_3$: 0.2694 g | D.I. water: 9 mL |
| $Na_2SiO_3$: 0.224505 g | D.I. water: 9 mL |
| $Na_2SiO_3$: 0.19457 g | D.I. water: 9 mL |
| $Na_2SiO_3$: 0.1796 g | D.I. water: 9 mL |

3. Washing Step.

The beads were then removed from fixing solution and were immersed into 1L of water at 50° C. The water layer above the beads was gently stirred overnight. The wash water was decanted the next day and replaced with another 1 L portion of water. The washing/decanting procedure was carried out a total of 3 times to decrease content of chlorine ions to around 50 ppm, wherein the final decant gives a negative result to a silver nitrate test.

4. Drying Step.

The impregnated support was then dried for fifteen hours at 95° C. in a forced air oven.

5. Reduction Step.

The reduction procedure was carried out in a glass or quartz tube heated with a tube furnace. 3.1 g of each catalyst precursor were heated in a nitrogen flow (rate 300–330 ml/min) from room temperature to 150° C. for one hour. The beads were further heated in a nitrogen flow to 300° C. for a half hour. Adsorbed water evolved during this heating period. The nitrogen flow was maintained and a 5% volume of ethylene in nitrogen mixture was introduced at a flow of 300–330 ml/min. After 1.5 hours of reduction at 300° C., the 5% ethylene in nitrogen mixture was turned off leaving the pure nitrogen flow. The beads were then cooled to room temperature under nitrogen.

6. Promoting Step.

Reduced impregnated support was promoted with 6–7 wt. % of potassium acetate (KOAc) by incipient wetness technique. Beads were placed into a flask.

7. Final Drying Step.

The catalyst was placed in an oven at room temperature. The temperature was increased to 120° C. The catalyst was dried at 120° C. for one hour in a nitrogen flow.

TABLE 6

Amount of Fixing Agent (1.2–2.1 Molar Excess)

| Example # | Pd Wt. % Calculated (Actual) | Au Wt. % Calculated (Actual) | Reaction Temp. °C. | VA Selectivity (%) | Space Time Yield (50 psig) | Expected Space Time Yield @ 120 psig |
|---|---|---|---|---|---|---|
| Example 21 (2.1 XS) | 0.63 (0.67)* | 0.52 (0.28)* | 140 | 93.3 | 310 | 620 |
|  |  |  | 150 | 91.3 | 415 | 830 |
|  |  |  | 160 | 87.6 | 530 | 1060 |
| Example 22 (1.8 XS) | 0.63 (NA) | 0.52 (NA) | 140 | 93.7 | 290 | 580 |
|  |  |  | 150 | 91.7 | 415 | 830 |
|  |  |  | 160 | 88.8 | 530 | 1060 |
| Example 23 (1.5 XS) | 0.63 (0.59) (0.71)* | 0.52 (0.34) (0.40)* | 140 | 94.2 | 300 | 600 |
|  |  |  | 150 | 92.7 | 410 | 820 |
|  |  |  | 160 | 90.2 | 530 | 1060 |
| Example 24 (1.3 XS) | 0.63 (NA) | 0.52 (NA) | 140 | 94.5 | 260 | 520 |
|  |  |  | 150 | 93.3 | 375 | 750 |
|  |  |  | 160 | 91.2 | 495 | 990 |
| Example 25 (1.2 XS) | 0.63 (0.65)* | 0.52 (0.43)* | 140 | 94.2 | 230 | 460 |
|  |  |  | 150 | 93.1 | 365 | 730 |
|  |  |  | 160 | 91.0 | 490 | 980 |

*-ICP analysis was done for not promoted samples.

The catalyst were evaluated in the reactor in the conditions as described above. The results for VA selectivity and space time yield are shown in Table 6. The data illustrates the advantages of a catalyst having been synthesized with a molar excess of precipitating or fixing agent of 1.5 (Example 23) had the best performance when considering both VA selectivity and space time yield.

Fixing Time

Examples 26–29

3 hrs v. 15 hrs

1. Impregnation Step.

A solution of 0.9136 g of $HAuCl_4 \cdot 3H_2O$ and 1.6830 g of $K_2PdCl_4$ in 47 ml of DI water was used to impregnate 80.0675 g of KA-160 at room temperature (R.T.) by an incipient wetness technique. The KA-160 was placed in a one-liter round bottom flask. After pouring the solution over the KA-160, the flask was connected to a rotary evaporator. The flask was then rotated slowly for one hour until all the solution was adsorbed by the support. After this, rotation was stopped and the impregnated support was left undisturbed for at least 1 hour. During that time the flask with impregnated support was stoppered to prevent solution evaporation from the surface of support.

2. Fixing Step.

Example 26

0.2392 g of $Na_2SiO_3$ was dissolved in 7.5 ml of D.I. water. One-eighth of the impregnated support from step 1 was reacted with the fixing solution by pouring the fixing solution over the beads. The mixture was placed in a beaker and sealed. The fixing reaction was allowed to proceed for 3 hours at room temperature. This procedure was repeated for the following:

Example 28

$Na_2SiO_3$: 0.3288 g D.I. water: 7.5 mL

Examples 27 and 29

The same procedure for Examples 26 and 28 was followed except the fixing reaction was allowed to proceed for 15 hours at room temperature.

3. Washing Step.

Examples 26 and 28

The beads were then removed from fixing solution and were immersed into 1L of water at 45–50° C. The water layer above the beads was gently stirred overnight. The wash water was decanted the next day and replaced with another 1L portion of water. The washing/decanting procedure was carried out a total of 4 times to decrease content of chlorine ions to around 50 ppm, wherein the final decant gives a negative result to a silver nitrate test.

Examples 27 and 29

The same procedure for Examples 26 and 28 was followed except the washing/decanting procedure was carried out a total of 3 times.

4. Drying Step.

The impregnated supports for each example were then dried overnight at 95° C. in a forced air oven.

5. Reduction Step.

For each example, the reduction procedure was carried out in a glass or quartz tube heated with a tube furnace. 4.6 g of each catalyst precursor were heated in a nitrogen flow (rate 300–330 ml/min) from room temperature to 150° C. for one hour. The beads were further heated in a nitrogen flow to 300° C. for a half hour. The nitrogen flow was maintained and a 5% volume of ethylene in nitrogen mixture was introduced at a flow of 300–330 ml/min. After 1 hour of reduction, the 5% ethylene in nitrogen mixture was turned off leaving the pure nitrogen flow. The beads were then cooled to room temperature under nitrogen.

6. Promoting Step.

For each example, the reduced impreganated supports were promoted with 6–7 wt. % of potassium acetate (KOAc) by incipient wetness technique. Beads were placed into a flask.

7. Final Drying Step.

The catalysts of each example were placed in an oven at room temperature. The temperature was increased to 120° C. the catalyst was dried at 120° C. for seventy minutes in a nitrogen flow.

TABLE 7

Fixing Time (3 Hours v. 15 Hours)

| Example # | Pd Wt. % Calculated (Actual) | Au Wt. % Calculated (Actual) | Reaction Temp. °C. | VA Selectivity (%) | Space Time Yield (50 psig) | Expected Space Time Yield @ 120 psig |
|---|---|---|---|---|---|---|
| Example 26 (3 hrs) | 0.63 | 0.52 | 140 | 93.6 | 255 | 510 |
|  |  |  | 150 | 92.0 | 370 | 740 |
|  |  |  | 160 | 88.5 | 500 | 1000 |
| Example 27 (15 hrs) | 0.63 | 0.52 | 140 | 93.6 | 270 | 540 |
|  |  |  | 150 | 92.0 | 380 | 760 |
|  |  |  | 160 | 89.2 | 490 | 980 |
| Example 28 (3 hrs) | 0.63 | 0.52 | 140 | 92.8 | 220 | 440 |
|  |  |  | 150 | 90.9 | 325 | 650 |
|  |  |  | 160 | 88.2 | 395 | 790 |
| Example 29 (15 hrs) | 0.63 | 0.52 | 140 | 93.0 | 240 | 480 |
|  |  |  | 150 | 90.5 | 330 | 660 |
|  |  |  | 160 | 87.4 | 420 | 840 |

The catalysts were evaluated in the reactor in the conditions as described above. The results for VA selectivity and space time yield are shown in Table 7. The data illustrates the advantages of a catalyst having a fixing time of at least three hours. It is further noted that the catalysts of Example 27 and 29 (fifteen hours) have better space time yield than the catalysts of Examples 26 and 28.

Examples 30–32
1 day v. 2 days v. 3 days
1. Impregnation Step.

A solution of 0.6852 g of $HAuCl_4 \cdot 3H_2O$ and 1.2622 g of $K_2PdCl_4$ in 36.3 ml of DI water was used to impregnate 60 g of KA-160 at room temperature (R.T.) by an incipient wetness technique. The KA-160 was placed in a one-liter round bottom flask. After pouring the solution over the KA-160, the flask was connected to a rotary evaporator. The flask was then rotated for ten minutes until all the solution was adsorbed by the support. After this, rotation was stopped and the impregnated support was left undisturbed for at least 1 hour. During that time the flask with impregnated support was stoppered to prevent solution evaporation from the surface of support.

2. Fixing Step.

Example 30

1.3897 g of $Na_2SiO_3$ was dissolved in 120 ml of D.I. water (pH=12.9) One-sixth of the impregnated support from step 1 was reacted with one-sixth of the fixing solution by pouring the fixing solution over the beads. The mixture was placed in a beaker and sealed. The fixing reaction was allowed to proceed for 24 hours at room temperature (pH= 8.22). This procedure was repeated for the following:

| Example 31: | Fixing time: 48 hours | pH: 7.98 |
|---|---|---|
| Example 32: | Fixing time: 72 hours | pH: 7.75 |

3. Washing Step.

Example 30

The beads were then removed from fixing solution and were immersed into 1L of water at 40° C. The water layer above the beads was gently stirred overnight. The wash water was decanted the next day and replaced with another 1L portion of water. The washing/decanting procedure was carried out a total of three times to decrease content of chlorine ions to around 50 ppm, wherein the final decant gives a negative result to a silver nitrate test.

Example 31

The same procedure for Example 30 was followed except the washing/decanting procedure was carried out once at 40° C. and twice at 50° C.

Example 32

The same procedure for Example 30 was followed except the washing/decanting procedure was carried out twice at 50° C.

4. Drying Step.

For each example, the impregnated supports were then dried for fourteen hours at 100° C. in a forced air oven.

5. Reduction Step.

Example 30

The reduction procedure was carried out in a glass or quartz tube heated with a tube furnace. 3.3 g of the catalyst precursor were heated in a nitrogen flow (rate 300–330 ml/min) from room temperature to 150° C. for a half hour. The beads were further heated in a nitrogen flow to 300° C. for twenty minutes. The nitrogen flow was maintained and a 5% volume of ethylene in nitrogen mixture was introduced at a flow of 300–330 ml/min. After 5 hours of reduction, the 5% ethylene in nitrogen mixture was turned off leaving the pure nitrogen flow. The beads were then cooled to room temperature under nitrogen.

Examples 31 and 32

The same procedure for Example 30 was followed except the beads were further heated in a nitrogen flow to 300° C. for twenty-five minutes.

6. Promoting Step.

For each example, the reduced impregnated supports were promoted with 6–7 wt. % of potassium acetate (KOAc) by incipient wetness technique. Beads were placed into a flask.

7. Final Drying Step.

Example 30

The catalyst was placed in an oven at room temperature. The temperature was increased to 120° C. The catalyst was dried at 120° C. for one hour in a nitrogen flow.

Examples 31 and 32

The catalysts were separately placed in an oven at room temperature. The temperature was increased to 100° C. The catalysts were dried at 100° C. for fourteen hours in a forced air oven.

TABLE 8

Fixing Time (1 day v. 2 days v. 3 days)

| Example # | Reaction Temp. ° C. | VA Selectivity (%) | Space Time Yield (50 psig) |
|---|---|---|---|
| Example 30 (1 day) | 140.0 | 92.9 | 174.7 |
| | 142.0 | 92.8 | 188.8 |
| | 142.0 | 92.7 | 195.5 |
| | 152.0 | 90.0 | 298.7 |
| | 153.0 | 89.9 | 309.2 |
| | 153.0 | 89.9 | 316.6 |
| | 161.0 | 97.2 | 392.1 |
| | 162.0 | 87.0 | 397.9 |
| | 162.0 | 87.0 | 399.5 |
| Example 31 (2 days) | 140.0 | 93.3 | 215.7 |
| | 141.5 | 93.6 | 229.6 |
| | 141.5 | 93.6 | 238.0 |
| | 151.5 | 91.8 | 323.9 |
| | 151.5 | 91.8 | 331.2 |
| | 151.5 | 91.7 | 324.9 |
| | 160.0 | 89.1 | 408.8 |
| | 162.5 | 88.4 | 439.1 |
| | 162.5 | 88.2 | 433.2 |
| Example 32 (3 days) | 139.0 | 93.3 | 227.0 |
| | 140.0 | 93.3 | 233.1 |
| | 141.0 | 93.4 | 239.4 |
| | 149.0 | 91.8 | 317.5 |
| | 149.0 | 91.8 | 321.2 |
| | 149.0 | 91.7 | 323.8 |
| | 160.0 | 87.6 | 441.9 |
| | 161.5 | 87.3 | 448.5 |
| | 161.5 | 87.2 | 450.9 |

The catalysts were evaluated in the reactor in the conditions as described above. The results for VA selectivity and space time yield are shown in Table 8. The data illustrates the advantages of a catalyst having a fixing time of three days. The catalyst of Example 32 has as good or better VA selectivity and consistently better space time yield as the catalysts of Examples 30 and 31.

Example 33 and Comparative Example 33A
Dry Fixing
1. Impregnation Step.

A solution of 0.6852 g of $HAuCl_4 \cdot 3H_2O$ and 1.2622 g of $K_2PdCl_4$ in 35.25 ml of DI water was used to impregnate 60 g of KA-160 at room temperature (R.T.) by an incipient wetness technique. The KA-160 was placed in a one-liter round bottom flask. After pouring the solution over the KA-160, the flask was connected to a rotary evaporator. The flask was then rotated for fifty minutes until all the solution was adsorbed by the support. After this, rotation was stopped and the impregnated support was left undisturbed for at least 1 hour. During that time the flask with impregnated support was stoppered to prevent solution evaporation from the surface of support.

2. Fixing Step.

Example 33

0.2316 g of $Na_2SiO_3$ was dissolved in 20 ml of D.I. water. One-sixth of the impregnated support from step 1 was reacted with the fixing solution by pouring the fixing solution over the beads. The mixture was placed in a beaker and sealed. The fixing reaction was allowed to proceed for 24 hours at room temperature

Example 33A 0.2361 g of powdered $Na_2SiO_3$ was placed into a round bottom flask. One-sixth of the impregnated support from step 1 was poured over the powder. The mixture was rotated for 20 minutes. The fixing reaction was allowed to proceed for 24 hours at room temperature 3. Washing Step.

For each example, the beads were then removed from fixing media and were immersed into 1L of water at 50° C. The water layer above the beads was gently stirred overnight. The wash water was decanted the next day and replaced with another 1L portion of water. The washing/decanting procedure was carried out a total of 3 times to decrease content of chlorine ions to around 50 ppm, wherein the final decant gives a negative result to a silver nitrate test.

4. Drying Step.

For each example, the impregnated supports were then dried for seventeen hours at 95° C. in a forced air oven.

5. Reduction Step.

For each example, the reduction procedure was carried out in a glass or quartz tube heated with a tube furnace. 6.5 g of each catalyst precursor were heated in a nitrogen flow (rate 300–330 ml/min) from room temperature to 150° C. for one hour. The beads were further heated in a nitrogen flow to 300° C. for a half hour. The nitrogen flow was maintained and a 5% volume of ethylene in nitrogen mixture was introduced at a flow of 300–330 ml/min. After 1 hour of reduction, the 5% ethylene in nitrogen mixture was turned off leaving the pure nitrogen flow. The beads were then cooled to room temperature under nitrogen.

6. Promoting Step.

For each example, the reduced impregnated supports were promoted with 6–7 wt. % of potassium acetate (KOAc) by incipient wetness technique. Beads were placed into a flask.

7. Final Drying Step.

The catalysts of each example were separately placed in an over at room temperature. The temperature was increased to 120° C. The catalysts were dried at 120° C. for one hour in a nitrogen flow.

TABLE 9

"Wet" v. "Dry" Fixing

| Example # | Pd Wt. % Calculated (Actual) | Au Wt. % Calculated (Actual) | Reaction Temp. ° C. | VA Selectivity (%) | Space Time Yield (50 psig) | Expected Space Time Yield @ 120 psig |
|---|---|---|---|---|---|---|
| Comparative Example 33A (solution) | 0.63 (0.56) | 0.52 (0.18) | 140 | 93.4 | 255 | 510 |
| | | | 150 | 92.0 | 340 | 680 |
| | | | 160 | 89.2 | 440 | 880 |

TABLE 9-continued

"Wet" v. "Dry" Fixing

| Example # | Pd Wt. % Calculated (Actual) | Au Wt. % Calculated (Actual) | Reaction Temp. ° C. | VA Selectivity (%) | Space Time Yield (50 psig) | Expected Space Time Yield @ 120 psig |
|---|---|---|---|---|---|---|
| Example 33 (dry) | 0.63 (0.59) | 0.52 (0.36) | 140 | 94.0 | 280 | 560 |
| | | | 150 | 92.6 | 385 | 770 |
| | | | 160 | 89.8 | 490 | 980 |

The catalysts were evaluated in the reactor in the conditions as described above. The results for VA selectivity and space time yield are shown in Table 9. The data illustrates the advantages of a catalyst synthesized with a "dry" or powder of precipitating or fixing agent rather than an aqueous solution. The catalyst of Example 33 has as good or better VA selectivity and consistently better space time yield as the catalyst of Comparative Example 33A.

Water Wash of Catalyst Precursor at 40–100° C.

Examples 34–39 and Comparative Examples 34A and 35A

1. Impregnation Step
A solution of 0.7999 g of $HAuCl_4 3H_2O$ and 1.4728 g of $K_2PdCl_4$ in 36.12 mL of DI water was used to impregnate 70 g of KA-160 at room temperature by an incipient wetness technique. The KA-160 was placed in a round bottom flask of glass with UV-protection. After pouring the solution over the KA-160, the flask was connected to a rotary evaporator. The flask was rotated for 5 minutes.

2. Fixing Step
The impregnated beads were transferred to a flat bottom flask of glass covered with aluminum foil for UV-protection. The fixing solution of $Na_2SiO_3$ (1.5691 g in 52.5 mL of water) was poured over the beads. The solution was rotated for 10 minutes at room temperature and then left overnight (15 hours) in a dark cabinet.

3. Washing Step

Comparative Example 34A

The beads was washed by immersing them in 1 L of D.I. water at room temperature. The water layer above the bead was gently stirred for approximately 24 hours. The water was decanted and replaced with another 1 L of D.I. water. This procedure was repeated for a total of four washes.

Example 34

The procedure for Comparative Example 34A was followed except at 40° C. and for a total of three washes.

Example 35

The procedure for Comparative Example 34A was followed except at 50° C. and for a total of three washes.

Example 36

The procedure for Comparative Example 34A was followed except at 60° C. and for a total of three washes.

Example 37

The procedure for Comparative Example 34A was followed except at 70° C. and for a total of three washes.

Example 38

The procedure for Comparative Example 34A was followed except at 80° C. and for a total of three washes.

Example 35A

The procedure for Comparative Example 34A was followed except at 100° C. and for a total of three washes.

4. Drying Step
The beads were dried at 95° C. for fifteen hours in a forced air oven.

5. Reduction Step
Reduction for each example was carried out in a glass or quartz tube heated with a tube furnace. The beads were heated in nitrogen at 150° C. for one hour and then heated further by a nitrogen flow which increased the temperature to 300° C. and held at that temperature for a half hour in nitrogen and for one hour in a ethylene/nitrogen flow. The beads were cooled to room temperature in nitrogen.

6. Promoting Step
The reduced samples were promoted with 7 wt. % potassium acetate (a solution of 0.1673 g of KOAc in 1.4337 mL of D.I. water) by incipient wetness.

7. Final Drying Step.
The catalysts were placed in an oven at room temperature. The temperature was increased to 120° C. The catalysts were dried at 120° C. for one hour in nitrogen.

TABLE 10

Wash Temperature

| Example # | Reaction Temp. ° C. | VA Selectivity (%) | Space Time Yield (50 psig) |
|---|---|---|---|
| Comparative Example 34A (RT) | 138.0 | 95.0 | 296.1 |
| | 138.0 | 94.9 | 302.6 |
| | 139.0 | 94.8 | 306.3 |
| | 149.0 | 93.3 | 409.6 |
| | 149.0 | 93.3 | 414.5 |
| | 149.0 | 93.4 | 410.6 |
| | 158.0 | 91.1 | 497.4 |
| | 158.0 | 91.0 | 495.8 |
| | 158.0 | 91.1 | 494.8 |
| Example 34A (40 C. Wash) | 139.0 | 94.6 | 299.9 |
| | 139.0 | 94.7 | 306.6 |
| | 139.0 | 94.7 | 309.5 |
| | 148.0 | 93.3 | 385.6 |
| | 149.0 | 93.2 | 401.2 |
| | 149.0 | 93.1 | 401.3 |
| | 158.0 | 90.9 | 474.0 |
| | 158.0 | 90.8 | 476.3 |
| | 158.0 | 90.7 | 480.6 |
| Example 35 (50 C. Wash) | 140.0 | 94.8 | 358.8 |
| | 141.5 | 94.5 | 353.7 |
| | 141.5 | 94.7 | 353.6 |
| | 148.0 | 93.4 | 451.8 |

TABLE 10-continued

Wash Temperature

| Example # | Reaction Temp. °C. | VA Selectivity (%) | Space Time Yield (50 psig) |
|---|---|---|---|
| | 148.0 | 93.4 | 448.9 |
| | 148.0 | 93.4 | 438.5 |
| | 158.0 | 90.6 | 538.7 |
| | 158.0 | 90.7 | 542.4 |
| | 158.0 | 90.8 | 538.5 |
| Example 36 | 141.5 | 94.9 | 349.1 |
| (60 C. Wash) | 141.5 | 94.9 | 360.6 |
| | 141.5 | 94.8 | 354.5 |
| | 149.5 | 93.7 | 475.5 |
| | 149.5 | 93.6 | 457.0 |
| | 149.5 | 93.6 | 457.0 |
| | 159.0 | 91.6 | 546.1 |
| | 160.0 | 91.3 | 550.4 |
| | 160.0 | 91.4 | 548.0 |
| Example 37 | 140.0 | 94.9 | 340.4 |
| (70 C. Wash) | 141.5 | 94.7 | 351.5 |
| | 141.5 | 94.9 | 348.4 |
| | 149.0 | 93.8 | 427.7 |
| | 149.0 | 93.7 | 431.5 |
| | 149.0 | 93.8 | 425.8 |
| | 159.5 | 91.3 | 530.8 |
| | 159.0 | 91.1 | 523.4 |
| | 159.0 | 91.3 | 523.0 |
| Example 38 | 141.0 | 94.9 | 342.2 |
| (80 C. Wash) | 141.5 | 95.0 | 341.7 |
| | 141.5 | 95.0 | 346.3 |
| | 148.0 | 94.0 | 412.0 |
| | 148.0 | 94.2 | 413.2 |
| | 148.0 | 94.2 | 416.7 |
| | 159.0 | 91.7 | 530.7 |
| | 159.5 | 91.6 | 524.9 |
| | 159.5 | 91.6 | 528.7 |
| Comparative | 137.5 | 94.5 | 269.8 |
| Example 35A | 137.5 | 94.6 | 270.5 |
| (100 C. Wash) | 137.5 | 94.6 | 269.1 |
| | 148.0 | 93.1 | 365.8 |
| | 149.0 | 93.0 | 381.0 |
| | 149.0 | 93.0 | 372.6 |
| | 158.0 | 90.1 | 469.7 |
| | 159.5 | 90.2 | 470.8 |
| | 159.5 | 90.1 | 470.6 |

The catalysts were evaluated in the reactor in the conditions as described above. The results for VA selectivity and space time yield are shown in Table 10. The data illustrates the advantages of a catalyst having a wash at 50–80° C., preferably 50–60° C. The catalyst of Examples 34–38 has as good or better VA selectivity and consistently better space time yield as the catalyst of Comparative Examples 34A and 35A.

Reduction in Nitrogen

Example 39–42

1. Impregnation Step.

A solution of 0.3426 g of $HAuCl_4 \cdot 3H_2O$ and 0.6312 g of $K_2PdCl_4$ in 15.66 g of DI water was used to impregnate 30.044 g of KA-160 at room temperature (R.T.) by an incipient wetness technique. The KA-160 was placed in a 0.5 liter round bottom flask. After pouring the solution over the KA-160, the flask was connected to a rotary evaporator. The flask was then rotated for ten minutes until all the solution was adsorbed by the support.

2. Fixing Step.

0.6735 g of $Na_2SiO_3$ was dissolved in 27 ml of D.I. water. The impregnated supports from step 1 were reacted with the fixing solution by pouring the fixing solution over the beads. The mixture was placed in a beaker and rotated for ten minutes. The beaker was placed in a dark cabinet. The fixing reaction was allowed to proceed for 24 hours at room temperature 3. Washing Step.

The beads were then removed from fixing media and were immersed into 1L of water at 50° C. The water layer above the beads was gently stirred overnight. The wash water was decanted the next day and replaced with another 1L portion of water. The washing/decanting procedure was carried out a total of 4 times to decrease content of chlorine ions to around 50 ppm, wherein the final decant gives a negative result to a silver nitrate test.

4. Drying Step.

The impregnated supports were then dried for fifteen hours at 95° C. in a forced air oven.

5. Reduction Step

Example 39

The reduction procedure was carried out in a glass or quartz tube heated with a tube furnace. One portion of the catalyst precursor was heated in a nitrogen flow (rate 300–330 ml/min) from room temperature to 150° C. for one hour. The beads were further heated in a nitrogen flow to 300° C. for one hour. After 1 hour of reduction, the beads were then cooled to room temperature under nitrogen.

Example 40

The reducing procedure above was repeated for another portion of the catalyst precursor except it was reduced at 450° C.

Example 41

One portion of the catalyst precursor was heated in a nitrogen flow (rate 300–330 ml/min) from room temperature to 150° C. for one hour. The beads were further heated in a nitrogen flow to 300° C. for a half hour. The nitrogen flow was maintained and a 5% volume of hydrogen in nitrogen mixture was introduced at a flow of 300–330 ml/min. After 0.5 hour of reduction at 299° C., the 5% hydrogen in nitrogen mixture was turned off leaving the pure nitrogen flow. The beads were then cooled to room temperature under nitrogen.

6. Promoting Step.

The reduced impregnated supports were promoted with 6–7 wt. % of potassium acetate (KOAc) by incipient wetness technique. Beads were placed into a flask.

7. Final Drying Step

The catalysts were separately placed in an oven at room temperature. The temperature was increased to 120° C. The catalysts were dried at 120° C. for one hour in a nitrogen flow.

Example 42

1. Impregnation Step.

A solution of 0.571 g of $HAuCl_4 \cdot 3H_2O$ and 1.052 g of $K_2PdCl_4$ in 26.1 ml of DI water was used to impregnate 50 g of KA-160 at room temperature (R.T.) by an incipient wetness technique. The KA-160 was placed in a 0.5 liter round bottom flask. After pouring the solution over the KA-160, the flask was connected to a rotary evaporator. The flask was then rotated for ten minutes until all the solution was adsorbed by the support.

2. Fixing Step.

0.224505 g of $Na_2SiO_3$ was dissolved in 9 ml of D.I. water. The impregnated support from step 1 was reacted with the fixing solution by pouring the fixing solution over the beads. The mixture was placed in a beaker and rotated for five minutes. The beaker was placed in a dark cabinet. The fixing reaction was allowed to proceed for 24 hours at room temperature 3. Washing Step.

The beads were then removed from fixing media and were immersed into 1L of water at 50° C. The water layer above the beads was gently stirred overnight. The wash water was decanted the next day and replaced with another 1L portion of water. The washing/decanting procedure was carried out a total of three times to decrease content of chlorine ions to around 50 ppm, wherein the final decant gives a negative result to a silver nitrate test.

4. Drying Step.

The impregnated supports were then dried for fifteen hours at 95° C. in a forced air oven.

5. Reduction Step

The reduction procedure was carried out in a glass or quartz tube heated with a tube furnace. The catalyst precursor was heated in a nitrogen flow (rate 300–330 ml/min) from room temperature to 150° C. for one hour. The beads were further heated in a nitrogen flow to 300° C. for a half hour. The nitrogen flow was maintained and a 5% volume of ethylene in nitrogen mixture was introduced at a flow of 300–330 ml/min. After 1.5 hour of reduction at 300° C., the 5% ethylene in nitrogen mixture was turned off leaving the pure nitrogen flow. The beads were then cooled to room temperature under nitrogen.

6. Promoting Step.

The reduced impregnated supports were promoted with 6–7 wt. % of potassium acetate (KOAc) by incipient wetness technique. Beads were placed into a flask.

7. Final Drying Step.

The catalysts were separately placed in an oven at room temperature. The temperature was increased to 120° C. The catalyst was dried at 120° C. for one hour in a nitrogen flow.

TABLE 11

Reduction in Nitrogen, Ethylene, Hydrogen

| Example # | Reaction Temp. ° C. | VA Selectivity (%) | Space Time Yield (50 psig) |
|---|---|---|---|
| Example 39 (N2-300° C.) | 140.0 | 94.4 | 283.2 |
| | 140.0 | 94.5 | 284.3 |
| | 140.0 | 94.6 | 286.4 |
| | 151.5 | 92.9 | 423.8 |
| | 150.0 | 93.3 | 403.2 |
| | 150.0 | 93.3 | 404.9 |
| | 159.0 | 91.0 | 510.7 |
| | 160.0 | 90.8 | 521.3 |
| | 160.0 | 90.8 | 518.0 |
| Example 40 (N$_2$-450° C.) | 142.0 | 94.1 | 420.6 |
| | 141.5 | 94.3 | 407.3 |
| | 141.5 | 94.3 | 405.9 |
| | 149.0 | 92.8 | 500.9 |
| | 150.0 | 92.8 | 501.3 |
| | 149.0 | 92.8 | 497.5 |
| | 159.0 | 90.1 | 590.5 |
| | 161.5 | 89.6 | 601.3 |
| | 162.0 | 89.5 | 596.8 |
| | 162.0 | 89.6 | 595.5 |
| Example 41 (H$_2$-300° C.) | 140.0 | 95.1 | 386.6 |
| | 140.0 | 95.0 | 370.8 |
| | 140.0 | 95.1 | 362.6 |
| | 152.0 | 93.0 | 491.5 |
| | 151.0 | 93.7 | 462.2 |
| | 150.0 | 93.7 | 458.5 |
| | 159.0 | 91.6 | 557.3 |
| | 159.0 | 91.5 | 565.1 |
| | 159.0 | 91.6 | 560.5 |
| Example 42 (C$_2$H$_4$-300° C.) | 138.0 | 94.4 | 280.7 |
| | 138.0 | 94.6 | 284.4 |
| | 137.5 | 94.6 | 266.0 |
| | 148.0 | 93.0 | 394.5 |
| | 149.0 | 93.0 | 381.2 |
| | 149.5 | 92.9 | 407.2 |

TABLE 11-continued

Reduction in Nitrogen, Ethylene, Hydrogen

| Example # | Reaction Temp. ° C. | VA Selectivity (%) | Space Time Yield (50 psig) |
|---|---|---|---|
| | 160.0 | 89.6 | 536.0 |
| | 163.0 | 89.4 | 555.7 |
| | 162.0 | 89.7 | 552.4 |
| | 162.5 | 89.7 | 556.7 |

The catalysts were evaluated in the reactor in the conditions as described above. The results for VA selectivity and space time yield are shown in Table 11. The data illustrates the advantages of a catalyst reduced with nitrogen. The catalyst of Example 39 (nitrogen, 300° C.) has VA selectivity and space time yield between that for the catalysts of Examples 41 and 42 (hydrogen, 300° C., and ethylene, 300° C., respectively). By increasing the nitrogen reduction temperature to 450° C., the catalyst of Example 40 has VA selectivity and space time yield comparable to or exceeding that for the catalyst of Example 41 (hydrogen, 300° C.).

Amount of Promoting Agent

Examples 43–45 and Comparative Examples 39A and 39B

1. Impregnation Step

A solution of 0.5714 g of HAuCl$_4$3H$_2$O and 01.052 g of K$_2$PdCl$_4$ in 26.1 mL of DI water was used to impregnate 50 g of KA-160 at room temperature by an incipient wetness technique. The KA-160 was placed in a round bottom flask of glass. After pouring the solution over the KA-160, the flask was connected to a rotary evaporator. The flask was rotated for 10 minutes.

2. Fixing Step

The impregnated beads were transferred to a flat bottom flask of glass which had a magnetic stirrer. The fixing solution of Na$_2$SiO$_3$ (1.1208 g in 37.5 mL of water) was poured over the beads. The flask was rotated for 10 minutes and the sample was then transferred into a dark cabinet. The fixing reaction was allowed to proceed for 15 hours at room temperature.

3. Washing Step

The beads were washed by immersing them in 1 L of D.I. water at 50° C. The water layer above the bead was gently stirred for approximately 24 hours. The water was decanted and replaced with another 1 L of D.I. water. This procedure was repeated for a total of 4 washes.

4. Drying Step

The beads were dried at 95° C. for 15 hours in a forced air oven.

5. Reduction Step

Reduction was carried out in a glass or quartz tube heated with a tube furnace. The beads were heated in 150° C. for one hour by a nitrogen flow and then the temperature was increased to 300° C. and held at that temperature for a half hour in a nitrogen flow. The nitrogen flow was maintained and a 5% volume of ethylene in nitrogen mixture was introduced at a flow of 300–330 ml/min. After one hour of reduction, the 5% ethylene in nitrogen mixture was turned off leaving the pure nitrogen flow. The beads were cooled to room temperature in nitrogen.

6. Promoting Step

Reduced sample were promoted with potassium acetate by incipient wetness in the following amounts:

| Example | Reduced sample | KOAc | H₂O | wt. % KOAc* |
|---|---|---|---|---|
| 43A | 3.4768 g | 0.03476 g | 2.086 g | 1 |
| 44A | 3.5837 g | 0.1075 g | 2.174 g | 3 |
| 43 | 3.3239 g | 0.166 g | 1.972 g | 5 |
| 44 | 2.7838 g | 0.167 g | 1.6517 g | 6 |
| 45 | 2.7874 g | 0.195 g | 1.65 g | 7 |
| 46 | 2.8288 g | 0.2263 g | 1.6961 g | 8 |
| 47 | 2.7871 g | 0.2508 g | 1.6556 g | 9 |
| 48 | 2.7966 g | 0.2796 g | 1.6623 g | 10 |
| 49 | 3.3580 g | 0.4029 g | 1.99 g | 12 |

*wt. % based only on weight of reduced sample

7. Final Drying Step

The catalyst was placed in an oven at room temperature. The temperature was increased to 120° C. The catalyst was dried in a nitrogen flow at 120° C. for one hour.

TABLE 12

| | Wt. % of KOAc | | |
|---|---|---|---|
| Example # | Reaction Temp. ° C. | VA Selectivity (%) | Space Time Yield (50 psig) |
| Example 43A (1%) | 138.0 | 89.6 | 62.4 |
| | 138.0 | 89.0 | 62.8 |
| | 138.0 | 89.2 | 62.7 |
| | 149.0 | 84.5 | 81.9 |
| | 149.0 | 84.2 | 82.3 |
| | 158.0 | 80.2 | 100.6 |
| | 158.0 | 79.5 | 100.9 |
| | 158.0 | 79.6 | 102.2 |
| Example 44A (3%) | 138.0 | 93.0 | 114.0 |
| | 138.0 | 93.0 | 115.6 |
| | 139.0 | 92.9 | 117.9 |
| | 151.0 | 90.9 | 198.8 |
| | 149.0 | 91.2 | 175.2 |
| | 157.0 | 89.7 | 215.9 |
| | 157.0 | 89.6 | 222.4 |
| | 158.0 | 89.4 | 228.2 |
| Example 43 (5%) | 140.0 | 94.3 | 217.4 |
| | 140.0 | 94.3 | 226.6 |
| | 140.0 | 94.5 | 228.8 |
| | 151.5 | 92.7 | 332.0 |
| | 151.5 | 92.7 | 339.2 |
| | 151.5 | 92.7 | 340.9 |
| | 160.0 | 90.4 | 411.5 |
| | 160.0 | 90.4 | 418.4 |
| | 160.0 | 90.3 | 422.1 |
| Example 44 (6%) | 139.0 | 94.7 | 317.9 |
| | 139.0 | 94.8 | 323.0 |
| | 140.0 | 94.8 | 321.5 |
| | 150.0 | 93.2 | 428.3 |
| | 149.5 | 93.3 | 424.2 |
| | 149.5 | 93.3 | 420.2 |
| | 159.0 | 90.6 | 506.2 |
| | 159.5 | 90.6 | 508.7 |
| | 159.5 | 90.7 | 507.7 |
| Example 45 (7%) | 138.0 | 95.2 | 288.7 |
| | 139.0 | 95.1 | 311.9 |
| | 139.0 | 95.2 | 316.3 |
| | 150.0 | 93.7 | 438.3 |
| | 150.0 | 93.6 | 438.6 |
| | 150.0 | 93.6 | 440.5 |
| | 159.0 | 91.7 | 525.4 |
| | 159.0 | 91.8 | 527.8 |
| | 159.0 | 91.7 | 527.8 |
| Example 46 (8%) | 141.0 | 95.0 | 335.0 |
| | 141.5 | 95.1 | 341.5 |
| | 141.5 | 95.1 | 343.1 |
| | 149.0 | 93.9 | 429.2 |
| | 150.0 | 93.6 | 478.0 |
| | 150.0 | 93.8 | 436.3 |
| | 160.0 | 91.7 | 537.7 |
| | 160.0 | 91.5 | 541.7 |
| | 160.0 | 91.7 | 534.3 |
| Example 47 (9%) | 140.0 | 95.1 | 323.6 |
| | 140.0 | 95.1 | 325.7 |
| | 141.0 | 95.2 | 325.5 |
| | 149.0 | 94.6 | 411.6 |
| | 149.0 | 94.1 | 409.7 |
| | 149.0 | 94.2 | 409.6 |
| | 160.0 | 91.9 | 518.0 |
| | 160.0 | 91.7 | 521.8 |
| | 160.0 | 91.7 | 518.5 |
| Example 48 (10%) | 138.0 | 95.1 | 295.3 |
| | 140.0 | 95.1 | 301.7 |
| | 140.0 | 95.1 | 308.3 |
| | 148.0 | 94.1 | 386.2 |
| | 149.0 | 93.9 | 389.4 |
| | 149.0 | 94.0 | 384.4 |
| | 158.0 | 92.0 | 473.9 |
| | 158.0 | 91.9 | 470.8 |
| | 158.0 | 92.0 | 464.8 |
| Example 49 (12%) | 137.5 | 95.1 | 177.8 |
| | 138.0 | 95.2 | 180.7 |
| | 138.0 | 95.2 | 185.6 |
| | 148.0 | 93.9 | 257.8 |
| | 149.0 | 93.8 | 260.5 |
| | 149.0 | 94.0 | 262.7 |
| | 158.0 | 91.8 | 334.4 |
| | 158.0 | 91.7 | 336.9 |
| | 158.0 | 91.8 | 343.4 |

The catalysts were evaluated in the reactor in the conditions as described above. The results for VA selectivity and space time yield are shown in Table 12. The data illustrates the advantages of a catalyst promoted with potassium acetate in the range of from about 5 to about 12 wt. %, preferably about 6 to about 10 wt. %, more preferably about 7 to about 8 wt. %. The catalysts of Examples 43–49 have better VA selectivity space time yield than the catalysts of Comparatives Example 43A and 44A.

Final Drying in $N_2$

Example 50 and Comparative Example 50A

1. Impregnation Step

A solution of 0.6852 g of $HAuCl_4 3H_2O$ and 01.2622 g of $K_2PdCl_4$ in 35.25 mL of DI water was used to impregnate 60 g of KA-160 at room temperature by an incipient wetness technique. The KA-160 was placed in a round bottom flask of glass with UV-protection. After pouring the solution over the KA-160, the flask was connected to a rotary evaporator. The flask was rotated for 50 minutes. After the rotation was stopped, the impregnated support was let stand for one hour.

2. Fixing Step

The fixing solution of $Na_2SiO_3$ (0.2316 g in 20 mL of water) was poured over one-sixth of the beads. The solution was left for 24 hours at room temperature.

3. Washing Step

The beads were washed by immersing them in 1 L of D.I. water at 50° C. The water layer above the bead was gently stirred for approximately 24 hours. The water was decanted and replaced with another 1 L of D.I. water. This procedure was repeated for a total of three washes.

4. Drying Step

The beads were dried at 95° C. for 17 hours in a forced air oven.

5. Reduction Step

Reduction was carried out in a glass or quartz tube heated with a tube furnace. The beads were heated in 150° C. for one hour by a nitrogen flow and then the temperature was increased to 300° C. and held at that temperature for a half hour in a nitrogen flow. The nitrogen flow was maintained and a 5% volume of ethylene in nitrogen mixture was introduced at a flow of 300–330 ml/min. After one hour of reduction, the 5% ethylene in nitrogen mixture was turned off leaving the pure nitrogen flow. The beads were cooled to room temperature in nitrogen.

6. Promoting Step

The reduced sample was promoted with 7 wt. % potassium acetate by incipient wetness.

7. Final Drying Step

The catalyst was divided into two equal parts.

Example 50A

One part was placed in an oven at room temperature. The temperature was increased to 95° C. The catalyst was dried at 95° C. in a forced air oven for 17 hours.

Example 50

The other part was placed in an oven at room temperature. The temperature was increased to 120° C. The catalyst was dried in a nitrogen flow (35 ml/min) at 120° C. for one hour.

TABLE 13

Drying in Air v. Nitrogen

| Example # | Pd Wt. % Calculated (Actual) | Au Wt. % Calculated (Actual) | Reaction Temp. ° C. | VA Selectivity (%) | Space Time Yield (50 psig) | Expected Space Time Yield @ 120 psig |
|---|---|---|---|---|---|---|
| Comparative Example 50A (Air Dry) | 0.63 (0.56) | 0.52 (0.18) | 140 | 93.5 | 245 | 490 |
|  |  |  | 150 | 92.3 | 310 | 620 |
|  |  |  | 160 | 89.6 | 380 | 760 |
| Example 50 ($N_2$ Dry) | 0.632 (0.56) | 0.52 (0.18) | 140 | 93.4 | 255 | 510 |
|  |  |  | 150 | 92.0 | 340 | 680 |
|  |  |  | 160 | 89.2 | 440 | 880 |

The catalysts were evaluated in the reactor in the conditions as described above. The results for VA selectivity and space time yield are shown in Table 13. The data illustrates the advantages of a catalyst having a drying step in nitrogen rather than air. The catalyst of Example 50 has as good VA selectivity and consistently better space time yield as that for the catalyst of Comparative Example 50A.

What is claimed as new and desired to be secured by Letter of Patent is:

1. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:
   (a) impregnating the support particles with aqueous solutions of water-soluble palladium and gold compounds so that the weight ratio of palladium to gold is in the range from 2:8 to 8:2;
   (b) precipitating water-insoluble palladium and gold compounds onto the support particles using alkali metal silicates or hydroxides as a precipitating agent;
   (c) washing the precipitated support with water until a decant of said wash water is negative to a silver nitrate test;
   (d) drying the washed precipitated support;
   (e) heating the dried washed precipitated support in a flow of inert gas from room temperature to 150° C. holding the temperature at 150° C. for 0.5 to one hour and then increasing the temperature;
   (f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;
   (g) further impregnating the support particles with said potassium alkanoate to a point of incipient wetness of the support particles; and
   (h) drying the catalyst.

2. The process of claim 1 wherein the weight ratio of palladium to gold is in the range from 6:4 to 2:8.

3. The process of claim 1 wherein the weight ratio of palladium to gold is in the range from 8:2 to 5:5.

4. The process of claim 1 wherein the weight ratio of palladium to gold is in the range from 7:3 to 4:6.

5. The process of claim 1 wherein the weight ratio of palladium to gold is 6:4 to 5:5.

6. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:
   (a) impregnating the support particles with aqueous solutions of water-soluble palladium and gold compounds so that the volume of the impregnation solution corresponds to from 70 to 100% of the total pore volume of the support particles;
   (b) precipitating water-insoluble palladium and gold compounds onto the support particles using alkali metal silicates or hydroxides as a precipitating agent;
   (c) washing the precipitated support with water until a decant of said wash water is negative to a silver nitrate test;
   (d) drying the washed precipitated support;
   (e) heating the dried washed precipitated support in a flow of inert gas from room temperature to 150° C. holding the temperature at 150° C. for 0.5 to one hour and then increasing the temperature;
   (f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

7. The process of claim 6 wherein the volume of the impregnation solution corresponds to from 85 to 95% of the total pore volume of the support particles.

8. The process of claim 7 wherein the volume of the impregnation solution corresponds to about 90% of the total pore volume of the support particles.

9. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles from solutions using alkali metal silicates or hydroxides as a precipitating agent containing in 1.1 to 2.5 molar excess;

(c) washing the precipitated support with water until a decant of said wash water is negative to a silver nitrate test;

(d) drying the washed precipitated support;

(e) heating the dried washed precipitated support in a flow of inert gas from room temperature to 150° C., holding the temperature at 150° C. for 0.5 to one hour and then increasing the temperature;

(f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

10. The process of claim 9 wherein the precipitating agent in 1.2 to 2.1 molar excess.

11. The process of claim 10 wherein precipitating agent in about 1.5 molar excess.

12. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles using alkali metal silicates or hydroxides as a precipitating agent wherein the impregnated support is contacted with the precipitating agent for three hours up to seventy-two hours;

(c) washing the precipitated support with water until a decant of said wash water is negative to a silver nitrate test;

(d) drying the washed precipitated support;

(e) heating the dried washed precipitated support in a flow of inert gas from room temperature to 150° C., holding the temperature at 150° C. for 0.5 to one hour and then increasing the temperature;

(f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

13. The process of claim 12 wherein the impregnated support is contacted with the precipitating agent for fifteen hours up to seventy-two hours.

14. The process of claim 12 wherein the impregnated support is contacted with the precipitating agent for twenty-four hours up to seventy-two hours.

15. The process of claim 12 wherein the impregnated support is contacted with the precipitating agent for up to seventy-two hours.

16. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles with powders of alkali metal silicates or hydroxides as a precipitating agent;

(c) washing the precipitated support with water until a decant of said wash water is negative to a silver nitrate test;

(d) drying the washed precipitated support;

(e) heating the dried washed precipitated support in a flow of inert gas from room temperature to 150° C., holding the temperature at 150° C. for 0.5 to one hour and then increasing the temperature;

(f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

17. The process of claim 16 wherein the impregnated support is contacted with the precipitating agent for three hours to seventy-two hours.

18. The process of claim 16 wherein the impregnated support is contacted with the precipitating agent for twelve to thirty-six hours.

19. The process of claim 16 wherein the impregnated support is contacted with the precipitating agent for about twenty-four hours.

20. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles using alkali metal silicates or hydroxide as a precipitating agent in an environment protected from light;

(c) washing the precipitated support with water until a decant of said wash water is negative to a silver nitrate test;

(d) drying the washed precipitated support;

(e) heating the dried washed precipitated support in a flow of inert gas from room temperature to 150° C., holding the temperature at 150° C. for 0.5 to one hour and then increasing the temperature;

(f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

21. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles using alkali metal silicates or hydroxide as a precipitating agent;

(c) washing the precipitated support with water at a temperature of from 50 to 80° C. until a decant of said wash water is negative to a silver nitrate test;

(d) drying the washed precipitated support;

(e) heating the dried washed precipitated support in a flow of inert gas from room temperature to 150° C., holding the temperature at 150° C. for 0.5 to one hour and then increasing the temperature;

(f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;

(g) further impregnating the support particles with said potassium alkanoate to a point of incipient wetness of the support particles; and (h) drying the catalyst.

22. The process of claim 21 wherein the precipitated support is washed with water at a temperature of from 50 to 60° C.

23. The process of claim 21 wherein the precipitated support is washed with water at a temperature of about 50° C.

24. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:

(a) impregnating the support particles with aqueous solutions of water-soluble palladium and gold compounds;

(b) precipitating water-insoluble palladium and gold compounds onto the support particles using alkali metal silicates or hydroxide as a precipitating agent;

(c) washing the precipitated support with water until a decant of said wash water is negative to a silver nitrate test;

(d) drying the washed precipitated support;

(e) heating the dried washed precipitated support in a flow of inert gas from room temperature to 150° C., holding the temperature to 150° C. for 0.5 to one hour and then increasing the temperature;

(f) converting the precipitated water-insoluble palladium and gold compounds to palladium and gold on the support particles using nitrogen as a reducing agent at a temperature of greater than 150° C. up to 500° C.;

(g) further impregnating the support particles with said potassium alkanoate to a point of incipient wetness of the support particles; and (h) drying the catalyst.

25. The process of claim 24 wherein the reduction temperature is from 300 to 450° C.

26. The process of claim 24 wherein the support particles are impregnated with aqueous solutions of water-soluble palladium and gold compounds so that the weight ratio of palladium to gold is in the range from 2:8 to 8:2.

27. The process of claim 24 wherein the support particles are impregnated with aqueous solutions of water-soluble palladium and gold compounds so that the volume of the impregnation solution corresponds to from 70 to 100% of the total pore volume of the support particles.

28. The process of claim 24 wherein water-insoluble palladium and gold compounds are precipitated onto the support particles from solutions using alkali metal silicates or hydroxides as a precipitating agent containing in 1.1 to 2.5 molar excess.

29. The process of claim 24 wherein water-insoluble palladium and gold compounds are precipitated onto the support particles using alkali metal silicates or hydroxides as a precipitating agent wherein the impregnated support is contacted with the precipitating agent for three hours up to seventy-two hours.

30. The process of claim 24 wherein water-insoluble palladium and gold compounds are precipitated onto the support particles with powders of alkali metal silicates or hydroxides as a precipitating agent.

31. The process of claim 24 wherein water-insoluble palladium and gold compounds are precipitated onto the support particles using alkali metal silicates or hydroxides as a precipitating agent in an environment protected from light.

32. The process of claim 24 wherein the precipitated support is washed with water at a temperature of from 50 to 80° C. until a decant of said wash water is negative to a silver nitrate test.

33. The process of claim 24 wherein the support particles are further impregnated with said potassium alkanoate in a solution of 5–12 wt. % to a point of incipient wetness of the support particles.

34. The process of claim 24 wherein the catalyst is dried in nitrogen.

35. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:
   (a) impregnating the support particles with aqueous solutions of water-soluble palladium and gold compounds;
   (b) precipitating water-insoluble palladium and gold compounds onto the support particles using alkali metal silicates or hydroxide as a precipitating agent;
   (c) washing the precipitated support with water until a decant of said wash water is negative to a silver nitrate test;
   (d) drying the washed precipitated support;
   (e) heating the dried washed precipitated support in a flow of inert gas from room temperature to 150° C., holding the temperature at 150° C. for 0.5 to one hour and then increasing the temperature;
   (f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;
   (g) further impregnating the support particles with said potassium alkanoate in a solution of 5–12 wt. % to a point of incipient wetness of the support particles; and
   (h) drying the catalyst.

36. The process of claim 35 wherein said potassium alkanoate is in a solution of 6–10 wt. %.

37. The process of claim 35 wherein said potassium alkanoate is in a solution of 6–8 wt. %.

38. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps in the order of:
   (a) impregnating the support particles with aqueous solutions of water-soluble palladium and gold compounds;
   (b) precipitating water-insoluble palladium and gold compounds onto the support particles using alkali metal silicates or hydroxides as a precipitating agent;
   (c) washing the precipitated support with water until a decant of said wash water is negative to a silver nitrate test;
   (d) drying the washed precipitated support;
   (e) heating the dried washed precipitated support in a flow of inert as from room temperature to 150°C, holding the temperature at 150°C for 0.5 to one hour and then increasing the temperature;
   (f) converting the precipitated water-insoluble palladium and gold compounds to palladium and gold on the support particles using ethylene as a reducing agent at a temperature of greater than 150° C. up to 310° C., hydrogen as a reducing agent at a temperature of greater than 150° C. up to 299° C. or nitrogen as a reducing agent at a temperature of greater than 150° C. up to 500° C.;
   (g) further impregnating the support particles with said potassium alkanoate to a point of incipient wetness of the support particles; and
   (h) drying the catalyst in nitrogen.

39. The process of claim 38 wherein the catalyst is dried for one hour to twenty-four hours.

40. The process of claim 38 wherein the catalyst is dried at 95° C. to 150° C.

41. The process of claim 38 wherein the catalyst is dried at 95° C. to 120° C.

42. The process of claim 38 wherein the catalyst is dried at 120° C. for one hour.

* * * * *